(12) United States Patent
Safaei-Ghomi et al.

(10) Patent No.: US 11,332,434 B2
(45) Date of Patent: May 17, 2022

(54) SYNTHESIS OF LEVOMETHADONE HYDROCHLORIDE

(71) Applicants: Javad Safaei-Ghomi, Qom (IR); Mansoureh Naderi, Parand New Town (IR)

(72) Inventors: Javad Safaei-Ghomi, Qom (IR); Mansoureh Naderi, Parand New Town (IR)

( * ) Notice: Subject to any disclaimer, the term of this patent is extended or adjusted under 35 U.S.C. 154(b) by 183 days.

(21) Appl. No.: 16/841,805

(22) Filed: Apr. 7, 2020

(65) Prior Publication Data
US 2020/0277250 A1 Sep. 3, 2020

Related U.S. Application Data

(60) Provisional application No. 62/834,973, filed on Apr. 17, 2019.

(51) Int. Cl.
*C07C 209/66* (2006.01)
*C07C 209/46* (2006.01)
(52) U.S. Cl.
CPC .......... *C07C 209/66* (2013.01); *C07C 209/46* (2013.01)

(58) Field of Classification Search
None
See application file for complete search history.

(56) References Cited

U.S. PATENT DOCUMENTS

2017/0057909 A1* 3/2017 Mkrtchyan ........... C07C 221/00

OTHER PUBLICATIONS

Beckett et al. Journal of the Chemical Society, vol. 0, No. 0, Jan. 1, 1957, 858-861.*
Graff et al. J. Solution Chem (2017) 46; 25-43.*

* cited by examiner

*Primary Examiner* — Clinton A Brooks
(74) *Attorney, Agent, or Firm* — Bajwa IP Law Firm; Haris Zaheer Bajwa

(57) ABSTRACT

A method for synthesizing levomethadone hydrochloride including producing (R)-2-(dimethylamino)propan-1-ol by reducing N,N-dimethyl-D-alanine using borax, forming (R)-1-chloro-N,N-dimethylpropane-2-amine hydrochloride by chlorinating the (R)-2-(dimethylamino)propan-1-ol, synthesizing levomethadone nitrile hydrochloride by mixing the (R)-1-chloro-N,N-dimethylpropane-2-amine and diphenylacetonitrile with potassium t-butoxide and producing levomethadone hydrochloride by exposing the levomethadone nitrile hydrochloride to a Grignard reagent.

20 Claims, 32 Drawing Sheets

Forming a plurality of complexes including N, N-dimethyl-D-alanine and $NiCl_2 \cdot 6H_2O$ in water by adding $NiCl_2 \cdot 6H_2O$ to a solution of N, N-dimethyl-D-alanine ~ 116

↓

Mixing the plurality of complexes with water and borax ~ 118

SYNTHESIS OF LEVOMETHADONE HYDROCHLORIDE

CROSS-REFERENCE TO RELATED APPLICATION

This application claims the benefit of priority from U.S. Provisional Patent Application Ser. No. 62/834,973, filed on Apr. 17, 2019, and entitled "SYNTHESIS OF LEVOMETHADONE HYDROCHLORIDE," which is incorporated herein by reference in its entirety.

TECHNICAL FIELD

The present disclosure generally relates to levomethadone hydrochloride, particularly to a method for synthesizing levomethadone hydrochloride, and more particularly to a method for synthesizing levomethadone hydrochloride with high yield and high optical purity.

BACKGROUND

Levomethadone hydrochloride is a synthetic opioid used as an analgesic drug which is about 1.5 times to 2.4 times stronger than its racemic mixture. However, synthesis of the levomethadone hydrochloride faces several challenges. For example, conventional methods for producing levomethadone require several cooling and heating steps, hard and dangerous reaction conditions, and multiple refluxing steps that limit their industrial applicability.

Also, yield of the conventional methods is generally low due to the production of two different isomers. The reason for the formation of both isomers in conventional methods is the presence of the aziridinium chloride salt during the reaction. The aziridinium chloride salt as an intermediate molecule may be converted to an undesirable isomer and reduces the reaction yield for the desirable isomer. It should be noted that only isomer of (R)-2, 2-diphenyl-4-dimethyl-aminopentanenitrile or levomethadone nitrile may be useful for the synthesis of levomethadone hydrochloride.

Therefore, there is a need for a cost-effective method for the synthesis of levomethadone hydrochloride using cheap materials, green solvents with reaction conditions at ambient temperature without any need for using a nitrogen atmosphere, ice bath, and reflux conditions. Moreover, there is a need for an efficient method for the synthesis of levomethadone hydrochloride which may be used for producing only desirable isomer with high yield by preventing the formation of aziridinium chloride salt during the reaction.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for synthesizing levomethadone hydrochloride. In an exemplary embodiment, the method may include producing (R)-2-(dimethylamino)propan-1-ol by reducing N,N-dimethyl-D-alanine using borax, forming (R)-1-chloro-N,N-dimethylpropane-2-amine hydrochloride by chlorinating the (R)-2-(dimethylamino)propan-1-ol, synthesizing levomethadone nitrile hydrochloride by mixing the (R)-1-chloro-N,N-dimethylpropane-2-amine and diphenylacetonitrile with potassium t-butoxide, and producing levomethadone hydrochloride by exposing the levomethadone nitrile hydrochloride to a Grignard reagent.

In an exemplary embodiment, reducing the N,N-dimethyl-D-alanine using the borax may include forming a plurality of complexes in water by adding nickel chloride hexahydrate ($NiCl_2 \cdot 6H_2O$) to a solution of the N,N-dimethyl-D-alanine and mixing the plurality of complexes with water and borax. In an exemplary embodiment, the plurality of complexes may include the N,N-dimethyl-D-alanine and the $NiCl_2 \cdot 6H_2O$. In an exemplary embodiment, mixing the plurality of complexes with water and borax may include forming a solution by adding the plurality of complexes to water and adding borax to the solution.

In an exemplary embodiment, adding borax to the solution may include adding borax decahydrate ($Na_2B_4O_7 \cdot 10H_2O$) with a concentration between about 100 mM and about 160 mM to the solution. In an exemplary embodiment, adding the plurality of complexes to water may include adding the plurality of complexes to water with a volume ratio of the plurality of complexes to the water between about 80 and about 200. In an exemplary embodiment, adding the plurality of complexes to water may include adding the plurality of complexes to water with a pH level between about 6.8 and about and about 7.6.

In an exemplary embodiment, adding the $NiCl_2 \cdot 6H_2O$ to the solution of the N,N-dimethyl-D-alanine may include adding the $NiCl_2 \cdot 6H_2O$ to the solution of the N,N-dimethyl-D-alanine with a pH level between about 6.8 and about 7.6. In an exemplary embodiment, adding the $NiCl_2 \cdot 6H_2O$ to the solution of the N,N-dimethyl-D-alanine may include mixing the $NiCl_2 \cdot 6H_2O$ to the solution of N,N-dimethyl-D-alanine with a molar ratio of $NiCl_2 \cdot 6H_2O$ to the N,N-dimethyl-D-alanine between about 3.5 and about 4.5.

In an exemplary embodiment, mixing the plurality of complexes with water and borax may include mixing the plurality of complexes with water and the borax at room temperature. In an exemplary embodiment, mixing the plurality of complexes with water and borax may include mixing the plurality of complexes with water and borax for a time period between about 1.5 days and about 3 days.

In an exemplary embodiment, chlorinating the (R)-2-(dimethylamino)propan-1-ol may include preparing (R)-2-(dimethylamino) propane-1-ol with HCl trapped by mixing (R)-2-(dimethylamino)propan-1-ol with HCl, forming a first solution by dissolving the (R)-2-(dimethylamino) propane-1-ol with HCl trapped in chloroform, and forming a second solution by dropwise adding the first solution to a solution of thionyl chloride at room temperature. In an exemplary embodiment, the solution of thionyl chloride may include thionyl chloride and chloroform with a volume ratio of the thionyl chloride to the chloroform between about 0.75 and about 0.95. In an exemplary embodiment, mixing the (R)-2-(dimethylamino)propan-1-ol with the HCl may include mixing the (R)-2-(dimethylamino)propan-1-ol with a HCl solution with a concentration between about 32 wt. % and about 37 wt. %.

In an exemplary embodiment, mixing the (R)-2-(dimethylamino)propan-1-ol with the HCl may include dropwise adding the HCl to the (R)-2-(dimethylamino)propan-1-ol at room temperature during a time period between about 2 hours and about 4 hours. In an exemplary embodiment, adding the first solution to the solution of thionyl chloride may include adding the first solution to the solution of thionyl chloride for a time period between about 30 minutes and about 60 minutes under a nitrogen atmosphere.

In an exemplary embodiment, mixing the (R)-1-chloro-N,N-dimethylpropane-2-amine and the diphenylacetonitrile with the potassium t-butoxide may include forming a first mixture by mixing (R)-1-chloro-N, N-dimethylpropane-2-amine hydrochloride with dry dimethylformamide (DMF), forming a second mixture by dissolving the diphenylacetonitrile in the first mixture, and forming a third mixture by mixing the potassium t-butoxide with the second mixture. In an exemplary embodiment, mixing the (R)-1-chloro-N, N-dimethylpropane-2-amine hydrochloride with the dry DMF may include mixing the (R)-1-chloro-N, N-dimethylpropane-2-amine hydrochloride with a concentration between about 50 mM and about 70 mM with the dry DMFa. In an exemplary embodiment, mixing the (R)-1-chloro-N, N-dimethylpropane-2-amine hydrochloride with the dry DMF may include mixing the (R)-1-chloro-N, N-dimethylpropane-2-amine hydrochloride with the dry DMF at room temperature under a nitrogen atmosphere.

In an exemplary embodiment, mixing the potassium t-butoxide with the second mixture may include mixing potassium t-butoxide with a concentration between about 150 mM and about 300 mM with the second mixture. In an exemplary embodiment, mixing the potassium t-butoxide with the second mixture may include mixing potassium t-butoxide with the second mixture at a temperature of about 0° C. for a time period of between about 30 minutes and about 60 minutes. In an exemplary embodiment, exposing the levomethadone nitrile hydrochloride to the Grignard reagent may include preparing the Grignard reagent by reacting magnesium powder with ethyl bromide in dry tetrahydrofuran (THF) and forming a mixture by adding the Grignard reagent to a solution of the levomethadone nitrile hydrochloride.

Other exemplary systems, methods, features, and advantages of the implementations will be or will become, apparent to one of ordinary skill in the art upon examination of the following figures and detailed description. It is intended that all such additional systems, methods, features, and advantages be included within this description and this summary, be within the scope of the implementations and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 1C illustrates an exemplary method for producing (R)-2-(dimethylamino) propan-1-ol by reducing N,N-dimethyl-D-alanine using borax, consistent with one or more exemplary embodiments of the present disclosure.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Disclosed herein is an exemplary method for synthesizing levomethadone hydrochloride with high yield and optical purity. In an exemplary method, cost-effective compounds such as borax may be used which may not only decrease the costs and risks of the conventional methods but may also obviate the need for some refluxing, heating, and cooling steps which may be considered as obstacles in scaling up the methods for synthesizing levomethadone hydrochloride. The exemplary method may be considered as an efficient method for synthesis of levomethadone hydrochloride by producing only desirable isomer with high yield by preventing the formation of aziridinium chloride salt during the reaction.

Figure 1A:
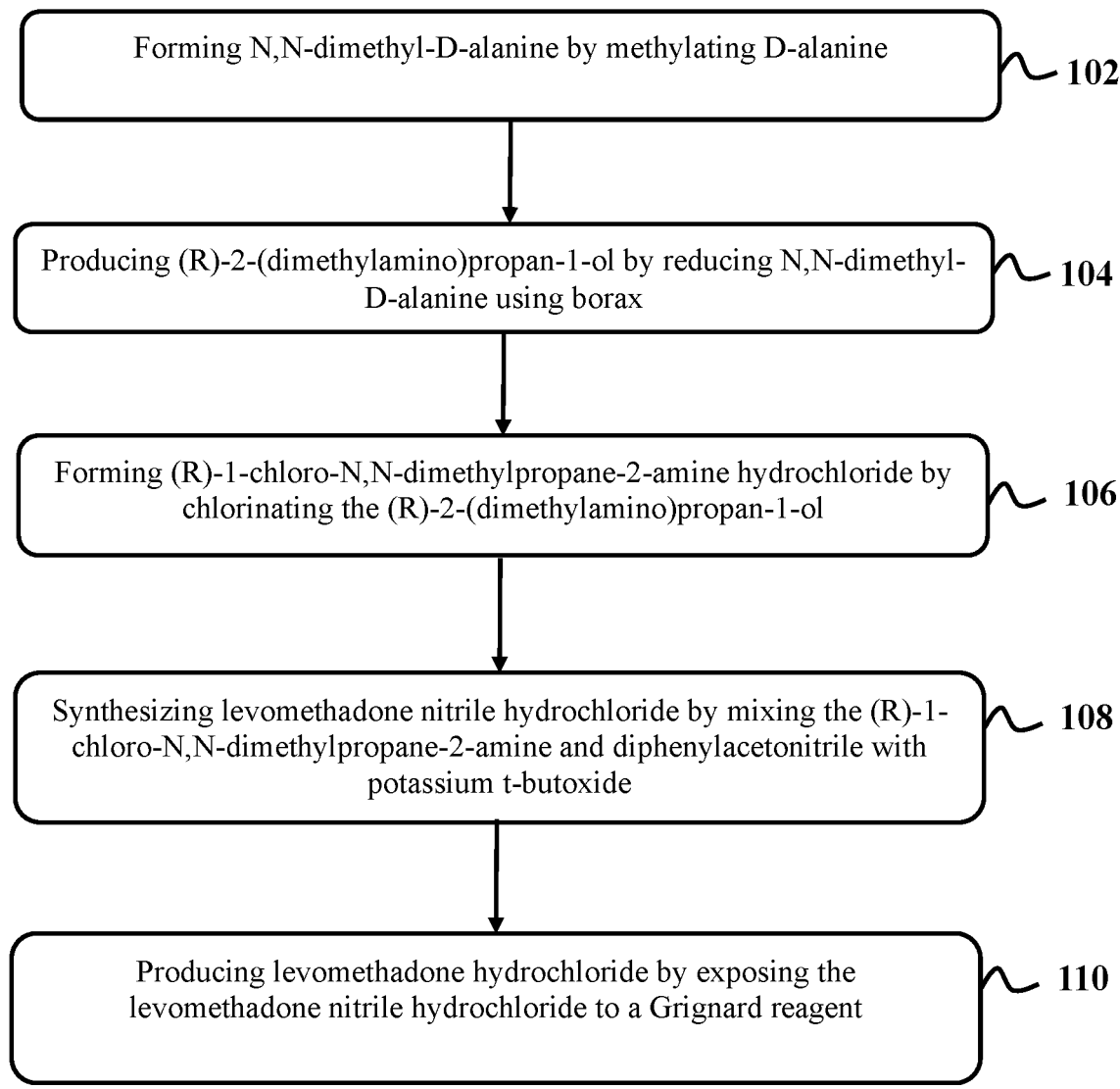
FIG. 1A shows a flowchart of an exemplary method for synthesizing levomethadone hydrochloride, consistent with one or more exemplary embodiments of the present disclosure.

FIG. 1A shows a flowchart of an exemplary method 100 for synthesizing levomethadone hydrochloride, consistent with one or more exemplary embodiments of the present disclosure. An exemplary method 100 may include forming N,N-dimethyl-D-alanine by methylating D-alanine (step 102), producing (R)-2-(dimethylamino) propan-1-ol by reducing the N,N-dimethyl-D-alanine using borax (step 104), forming (R)-1-chloro-N,N-dimethylpropane-2-amine hydrochloride by chlorinating the (R)-2-(dimethylamino) propan-1-ol (step 106), synthesizing levomethadone nitrile hydrochloride by mixing a solution of the (R)-1-chloro-N,N-dimethylpropane-2-amine hydrochloride and diphenylacetonitrile with potassium t-butoxide (step 108), and producing levomethadone hydrochloride by exposing the levomethadone nitrile hydrochloride to a Grignard reagent (step 110).

Figure 2A:
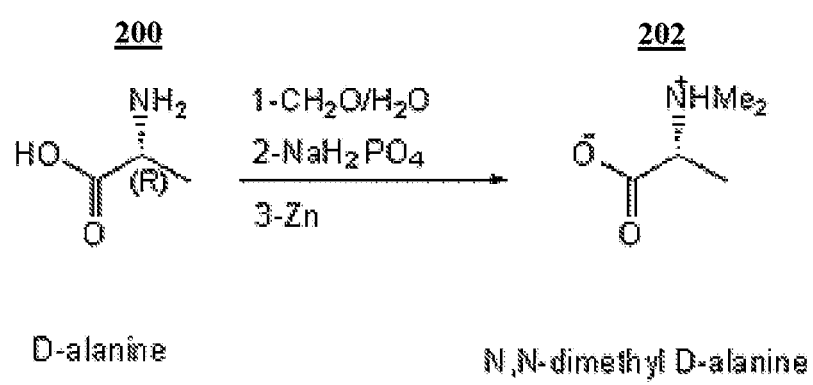
FIG. 2A illustrates a schematic representation for forming N,N-dimethyl-D-alanine, consistent with one or more exemplary embodiments of the present disclosure.

In further detail with respect to step 102, in an exemplary embodiment, the exemplary method may include forming N,N-dimethyl-D-alanine by methylating D-alanine. In the present disclosure, "methylating" may refer to an action of methylation that denotes adding a methyl group to D-alanine. FIG. 2A illustrates a schematic representation of step 102 for forming N,N-dimethyl-D-alanine 202 by methylating D-alanine 200, consistent with one or more exemplary embodiments of the present disclosure.

Figure 1B:
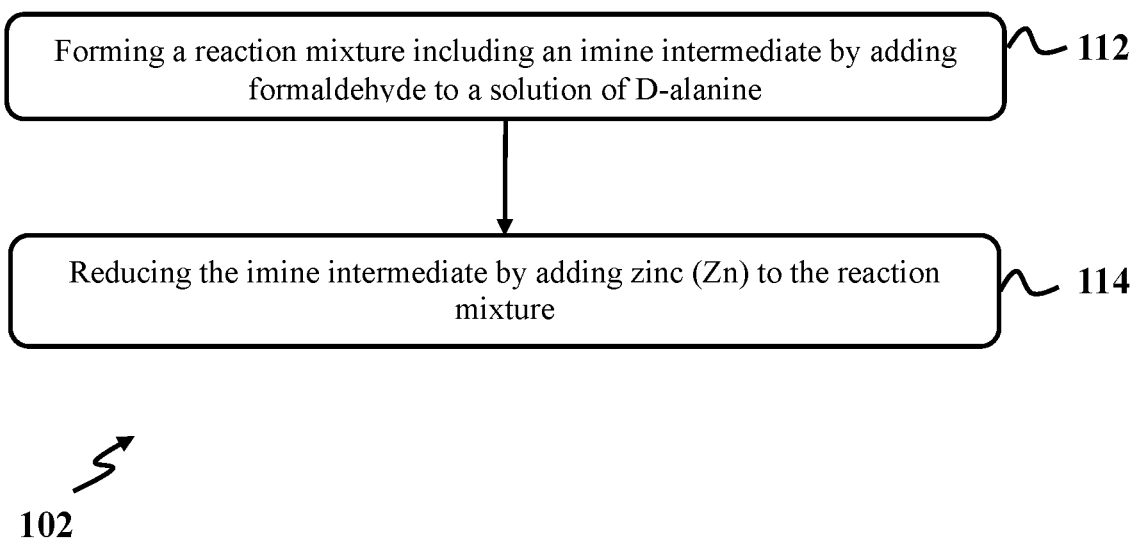
FIG. 1B illustrates an exemplary method for forming N,N-dimethyl-D-alanine by methylating D-alanine, consistent with one or more exemplary embodiments of the present disclosure.

FIG. 1B illustrates an exemplary method for forming N,N-dimethyl-D-alanine by methylating D-alanine, consistent with one or more exemplary embodiments of the present disclosure. Referring to FIG. 1B, forming the N,N-dimethyl-D-alanine by methylating D-alanine may include forming a reaction mixture, the reaction mixture including an imine intermediate by adding formaldehyde to a solution of D-alanine (step 112), and reducing the imine intermediate by adding zinc (Zn) to the reaction mixture (step 114).

In further detail with respect to step 112, in an exemplary embodiment, adding formaldehyde to the solution of D-alanine 200 may include adding a formaldehyde solution with a concentration of 37 wt. % to the solution of D-alanine 200. In an exemplary embodiment, the solution of D-alanine 200 may have a concentration of about 0.33 M. In an exemplary embodiment, adding the formaldehyde to the solution of D-alanine 200 may include adding the formaldehyde to the solution of D-alanine 200 with a molar ratio of the formaldehyde to the D-alanine between about 3.5 and about 4.5.

In an exemplary embodiment, forming the reaction mixture may further include adding sodium dihydrogen phosphate.2H$_2$O to the reaction mixture for adjusting pH to a pH level between about 4.9 and about 5.5. In an exemplary embodiment, adjusting pH to a pH level of about 5.25 may include adding sodium dihydrogen phosphate.2H$_2$O with an amount of about 36.9 mmoles to the reaction mixture. In an exemplary embodiment, the imine intermediate may include an iminium ion. In further detail with respect to step 114, adding Zn to the reaction mixture may include mixing Zn with the reaction mixture for a time period between about 45 minutes and about 75 minutes in a water bath at a temperature of about 20° C. In an exemplary embodiment, adding Zn to the reaction mixture may include adding Zn with a concentration between about 2 M and about 3 M to the reaction mixture.

Figure 2B:
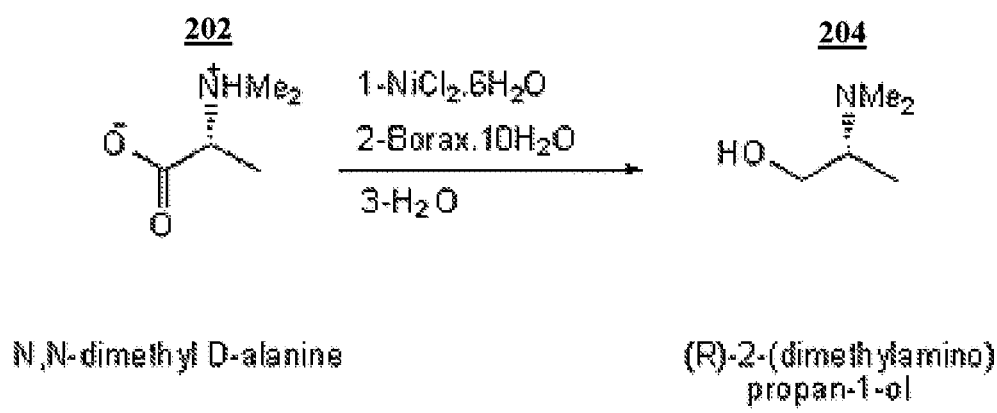
FIG. 2B illustrates a schematic representation for producing (R)-2-(dimethylamino) propan-1-ol, consistent with one or more exemplary embodiments of the present disclosure.

Referring back to FIG. 1A, in further detail with respect to step 104, in an exemplary embodiment, producing the (R)-2-(dimethylamino) propan-1-ol may include reducing the N,N-dimethyl-D-alanine using borax. FIG. 2B illustrates a schematic representation of step 104 for producing (R)-2-(dimethylamino) propan-1-ol 204, consistent with one or more exemplary embodiments of the present disclosure.

FIG. 1C illustrates an exemplary method for producing (R)-2-(dimethylamino) propan-1-ol by reducing N,N-dimethyl-D-alanine 202 using borax, consistent with one or more exemplary embodiments of the present disclosure. Referring to FIG. 1C, producing (R)-2-(dimethylamino) propan-1-ol 204 by reducing N,N-dimethyl-D-alanine 202 using borax may include forming a plurality of complexes including N, N-dimethyl-D-alanine 202 and $NiCl_2.6H_2O$ in water by adding $NiCl_2.6H_2O$ to a solution of N, N-dimethyl-D-alanine 202 (step 116) and mixing the plurality of complexes with water and borax (step 118).

In further detail with respect to step 116, in an exemplary embodiment, preparing a solution of N, N-dimethyl-D-alanine 202 may include preparing the solution of N, N-dimethyl-D-alanine 202 with a concentration of about 0.57 M by dissolving about 0.8536 mmoles of N, N-dimethyl-D-alanine 202 in 1.5 ml of deionized water. In an exemplary embodiment, adding the $NiCl_2.6H_2O$ to the solution of N, N-dimethyl-D-alanine 202 may include adding the $NiCl_2.6H_2O$ to the solution of N, N-dimethyl-D-alanine 202 with a molar ratio of $NiCl_2.6H_2O$ to the N, N-dimethyl-D-alanine 202 between about 3.5 and about 4.5. In an exemplary embodiment, adding the $NiCl_2.6H_2O$ to the solution of N, N-dimethyl-D-alanine 202 may include adding the $NiCl_2.6H_2O$ to the solution of N, N-dimethyl-D-alanine 202 in two sub-steps with a percentage between about 80% and about 90% for first sup-step and a percentage between about 10% and about 20% for second sub-step. In an exemplary embodiment, adding the $NiCl_2.6H_2O$ to the solution of N, N-dimethyl-D-alanine 202 in the two sub-steps may further include stirring the solution of N, N-dimethyl-D-alanine 202 between the two sub-steps for a time period between about 1.5 hours and about 2.5 hours at room temperature. In an exemplary embodiment, the solution of N, N-dimethyl-D-alanine 202 may have a pH level between about 6.8 and about 7.6.

In further detail with respect to step 118, in an exemplary embodiment, mixing the plurality of complexes with water and borax may include mixing the plurality of complexes with water and borax at room temperature for a time period between about 1.5 days and about 3 days. In an exemplary embodiment, mixing the plurality of complexes with water and borax may include mixing the plurality of complexes with water and borax decahydrate ($Na_2B_4O_7.10H_2O$).

In an exemplary embodiment, mixing the plurality of complexes with water and borax may include forming a solution by adding the plurality of complexes to water and adding borax to the solution. In an exemplary embodiment, adding the plurality of complexes to water may include adding the plurality of complexes to water with a volume ratio of the plurality of complexes to the water between about 80 and about 200. In an exemplary embodiment, adding the plurality of complexes to water may include adding the plurality of complexes to water with a pH level between 6.8 and 7.6. In an exemplary embodiment, adding borax to the solution may include adding borax decahydrate ($Na_2B_4O_7.10H_2O$) with a concentration between about 100 mM and about 160 mM to the solution. In an exemplary embodiment, producing (R)-2-(dimethylamino) propan-1-ol 204 may include reducing the N,N-dimethyl-D-alanine 202 using borax as a reducing agent in water as a solvent. In an exemplary embodiment, producing (R)-2-(dimethylamino) propan-1-ol 204 may include chemically reducing N,N-dimethyl-D-alanine 202 to the (R)-2-(dimethylamino) propan-1-ol using borax at room temperature. In an exemplary embodiment, producing (R)-2-(dimethylamino) propan-1-ol 204 may include chemically reducing N,N-dimethyl-D-alanine 202 to the (R)-2-(dimethylamino) propan-1-ol using borax without any need for using a reflux process, a heating process, and a nitrogen atmosphere.

In an exemplary embodiment, producing (R)-2-(dimethylamino) propan-1-ol 204 may further include extracting the (R)-2-(dimethylamino) propan-1-ol from the solution of (R)-2-(dimethylamino) propan-1-ol, forming dehydrated (R)-2-(dimethylamino) propan-1-ol, and purifying the dehydrated (R)-2-(dimethylamino) propan-1-ol. In an exemplary embodiment, the (R)-2-(dimethylamino) propan-1-ol may be extracted using chloroform. In an exemplary embodiment, dehydrated (R)-2-(dimethylamino) propan-1-ol may be formed using anhydrous magnesium sulfate. In an exemplary embodiment, the dehydrated (R)-2-(dimethylamino) propan-1-ol may be purified using a thick layer chromatography.

Figure 1D:
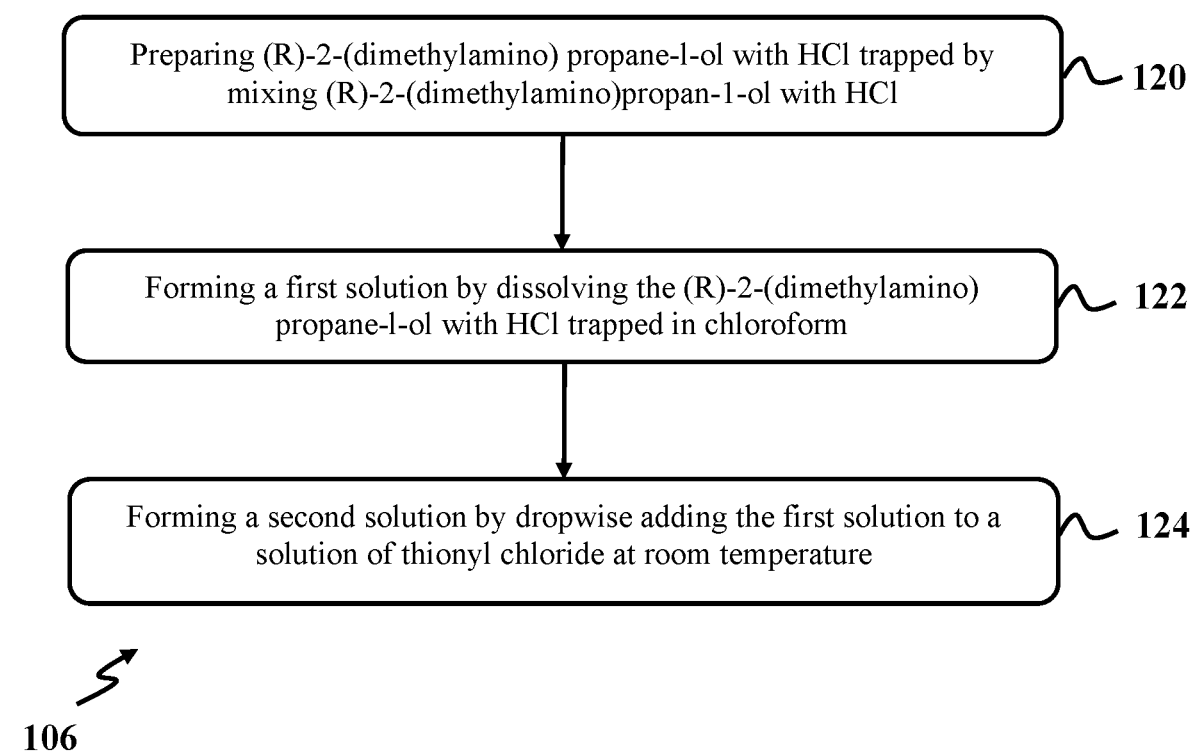
FIG. 1D illustrates an exemplary method for forming (R)-1-chloro-N,N-dimethylpropane-2-amine hydrochloride, consistent with one or more exemplary embodiments of the present disclosure.
Figure 2C:
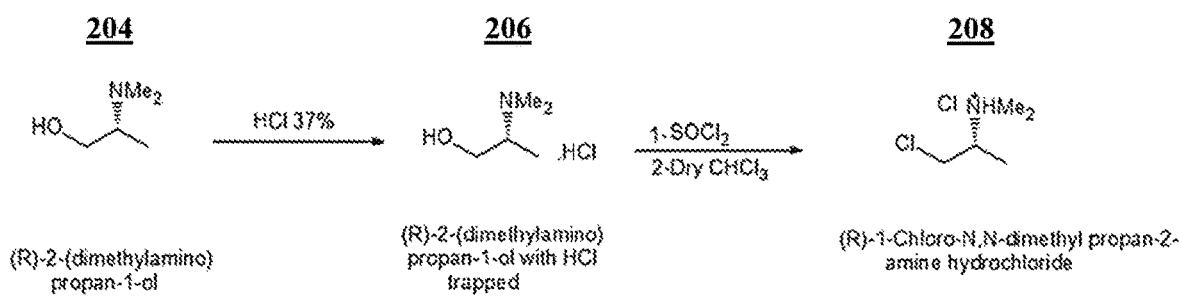
FIG. 2C illustrates a schematic representation for forming the (R)-1-chloro-N,N-dimethylpropane-2-amine hydrochloride, consistent with one or more exemplary embodiments of the present disclosure.

Referring back to FIG. 1A, in further detail with respect to step 106, in an exemplary embodiment, forming the (R)-1-chloro-N,N-dimethylpropane-2-amine hydrochloride may include chlorinating the (R)-2-(dimethylamino) propan-1-ol. FIG. 2C illustrates a schematic representation of step 106 for forming (R)-1-chloro-N,N-dimethylpropane-2-amine hydrochloride 208, consistent with one or more exemplary embodiments of the present disclosure. FIG. 1D illustrates an exemplary method for forming (R)-1-chloro-N,N-dimethylpropane-2-amine hydrochloride 208, consistent with one or more exemplary embodiments of the present disclosure.

Referring to FIG. 1D, chlorinating (R)-2-(dimethylamino) propan-1-ol 204 may include preparing (R)-2-(dimethylamino)propan-1-ol with HCl trapped 206 by mixing (R)-2-(dimethylamino)propan-1-ol 204 with HCl (step 120), forming a first solution by dissolving R)-2-(dimethylamino) propan-1-ol with HCl trapped 206 in chloroform (step 122), and forming a second solution by adding the first solution to a solution of thionyl chloride at room temperature (step 124). In an exemplary embodiment, chlorinating (R)-2-(dimethylamino)propan-1-ol 204 may be performed at room temperature without any need for using a reflux process and a heating process. In the present disclosure, "(R)-2-(dimethylamino) propane-1-ol with HCl trapped" may refer to a matrix including hydrochloric acid molecules trapped within (R)-2-(dimethylamino) propane-1-ol molecules.

In further detail with respect to step 120, preparing (R)-2-(dimethylamino)propan-1-ol with HCl trapped 206 may include mixing (R)-2-(dimethylamino)propan-1-ol 204 with a concentration between about 5.2 mM and about 7.2 mM with a HCl solution. In an exemplary embodiment, the HCl solution may have a concentration between about 32 wt. % and about 37 wt. %. In an exemplary embodiment, mixing (R)-2-(dimethylamino)propan-1-ol 204 with HCl may include dropwise adding HCl to (R)-2-(dimethylamino)propan-1-ol 204 at room temperature during a time period of between about 2 hours and about 4 hours. In an exemplary embodiment, mixing (R)-2-(dimethylamino)propan-1-ol 204 with HCl may further include stirring (R)-2-(dimethylamino)propan-1-ol 204 with HCl for about five (5) hours.

In further detail with respect to step 122, forming the first solution may include dissolving the R)-2-(dimethylamino) propan-1-ol with HCl trapped in chloroform. In an exemplary embodiment, dissolving the R)-2-(dimethylamino)propan-1-ol with HCl trapped 206 in chloroform may include dissolving the R)-2-(dimethylamino)propan-1-ol with HCl trapped 206 in dry chloroform under heating.

In further detail with respect to step 124, forming the second solution may include adding the first solution to a solution of thionyl chloride (SOCl$_2$). In an exemplary embodiment, adding the first solution to the solution of thionyl chloride may include dropwise adding the first solution to the solution of thionyl chloride. In an exemplary embodiment, the solution of thionyl chloride may include thionyl chloride and chloroform with a volume ratio of the thionyl chloride to the chloroform between about 0.75 and about 0.95. In an exemplary embodiment, adding the first solution to the solution of thionyl chloride may include adding the first solution to the solution of thionyl chloride with a volume ratio of the first solution to the solution of thionyl chloride between about 0.7 and about 0.9.

In an exemplary embodiment, adding the first solution to the solution of thionyl chloride may include adding the first solution to the solution of thionyl chloride at room temperature for a time period between about 30 minutes and about 60 minutes under a nitrogen atmosphere. In an exemplary embodiment, the second solution may be stirred at room temperature for about five (5) hours until forming a white precipitate. In an exemplary embodiment, thionyl chloride may be used as a chlorinating agent. In an exemplary embodiment, adding the first solution to the solution of thionyl chloride may be classified as a reaction with inverse addition which may be used instead of adding the solution of thionyl chloride to the first solution. In an exemplary embodiment, although adding the solution of thionyl chloride to the first solution may be an exothermic reaction, adding the first solution to the solution of thionyl chloride may not be an exothermic reaction and may overcome the need for utilizing any cooling systems, such as ice bath.

Figure 2D:
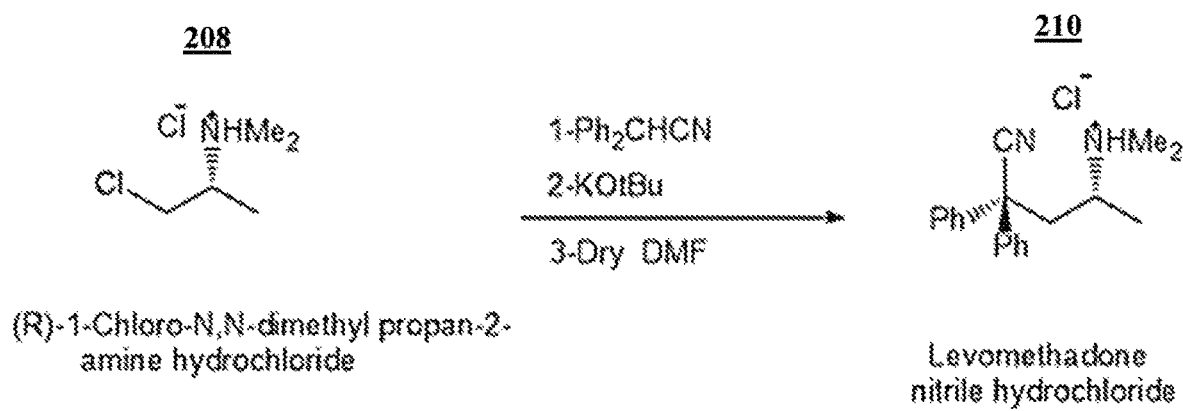
FIG. 2D illustrates a schematic representation for synthesizing the levomethadone nitrile hydrochloride, consistent with one or more exemplary embodiments of the present disclosure.

Referring back to FIG. 1A, in further detail with respect to step 108, in an exemplary embodiment, the exemplary method may include synthesizing the levomethadone nitrile hydrochloride by mixing (R)-1-chloro-N,N-dim ethyl propane-2-amine hydrochloride and diphenylacetonitrile with potassium t-butoxide. FIG. 2D illustrates a schematic representation of step 108 for synthesizing levomethadone nitrile hydrochloride 210, consistent with one or more exemplary embodiments of the present disclosure.

Figure 1E:
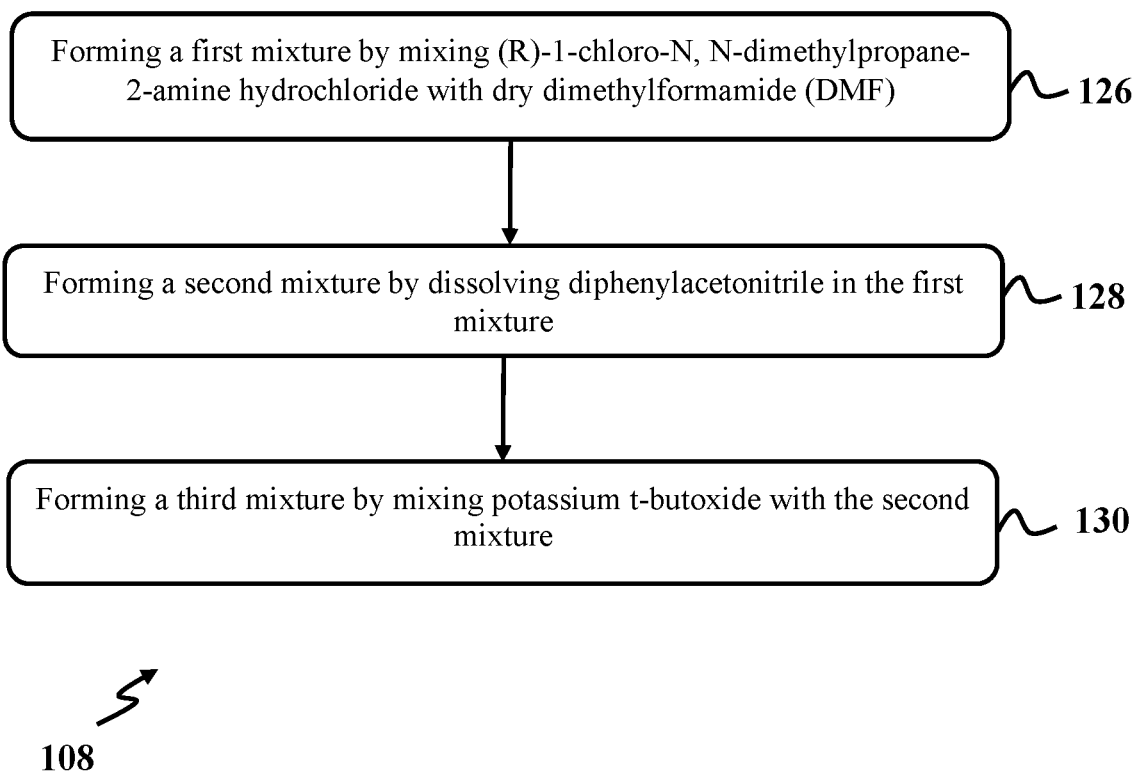
FIG. 1E illustrates an exemplary method for synthesizing levomethadone nitrile hydrochloride, consistent with one or more exemplary embodiments of the present disclosure.

FIG. 1E illustrates an exemplary method for synthesizing levomethadone nitrile hydrochloride 210, consistent with one or more exemplary embodiments of the present disclosure. Referring to FIG. 1E, synthesizing levomethadone nitrile hydrochloride 210 may include forming a first mixture by mixing (R)-1-chloro-N, N-dimethylpropane-2-amine hydrochloride 208 with dry dimethylformamide (DMF) (step 126), forming a second mixture by dissolving diphenylacetonitrile in the first mixture (step 128), and forming a third mixture by mixing potassium t-butoxide with the second mixture (step 130).

In an exemplary embodiment, performing step 108 for synthesizing the levomethadone nitrile hydrochloride from the R)-1-chloro-N,N-dimethylpropane-2-amine hydrochloride based on the order of the steps of FIG. 1E may prevent the formation of aziridinium chloride salt as an intermediate and may lead to the synthesis of the levomethadone nitrile hydrochloride as a desirable isomer with a yield of about 90%.

In further detail with respect to step 126, in an exemplary embodiment, forming the first mixture may include mixing (R)-1-chloro-N, N-dimethylpropane-2-amine hydrochloride 208 with a concentration between about 50 mM and about 70 mM with dry dimethylformamide (DMF). In an exemplary embodiment, mixing the (R)-1-chloro-N, N-dimethylpropane-2-amine hydrochloride with the dry DMF may include mixing the (R)-1-chloro-N, N-dimethylpropane-2-amine hydrochloride with the dry DMF at room temperature under a nitrogen atmosphere. In further detail with respect to step 128, in an exemplary embodiment, dissolving diphenylacetonitrile in the first mixture may include dissolving the diphenylacetonitrile in the first mixture at room temperature under a nitrogen atmosphere. In an exemplary embodiment, forming the second mixture may further include stirring the second mixture for a time period of about five (5) minutes, and cooling to 0° C. utilizing an ice-salt bath. In an exemplary embodiment, dissolving diphenylacetonitrile in the first mixture may include dissolving the diphenylacetonitrile with a concentration between about 155 mM and about 175 mM in the first mixture.

In further detail with respect to step 130, in an exemplary embodiment, forming the third mixture may include vigorously mixing potassium t-butoxide with the second mixture in a cooling bath at a temperature of about 0° C. for a time period between about 30 minutes and about 60 minutes until obtaining a yellow solution. In an exemplary embodiment, mixing the potassium t-butoxide with the second mixture may include mixing the potassium t-butoxide with a concentration between about 150 mM and about 300 Mm with the second mixture. In an exemplary embodiment, synthesizing levomethadone nitrile hydrochloride 210 may further include heating the third mixture to a temperature of about 58° C. for a time period of about fourteen (14) hours under a nitrogen atmosphere. In an exemplary embodiment, heating the third mixture to a temperature of about 58° C. may include placing the third mixture in an oil bath with a temperature of about 58° C.

In an exemplary embodiment, synthesizing levomethadone nitrile hydrochloride 210 may further include extracting the levomethadone nitrile hydrochloride from the third mixture, dehydrating the levomethadone nitrile hydrochloride, and purifying the levomethadone nitrile hydrochloride. In an exemplary embodiment, extracting the levomethadone nitrile hydrochloride from the third mixture may include extracting the levomethadone nitrile hydrochloride from the third mixture using ethyl acetate.

In an exemplary embodiment, dehydrating the levomethadone nitrile hydrochloride may include dehydrating the levomethadone nitrile hydrochloride using anhydrous sodium sulfate. In an exemplary embodiment, purifying the levomethadone nitrile hydrochloride may include purifying the levomethadone nitrile hydrochloride using a column chromatography technique. In an exemplary embodiment, purifying the levomethadone nitrile hydrochloride using a column chromatography technique may include using a solvent including n-hexane and ethyl acetate with a ratio of 9:1.

Figure 1F:
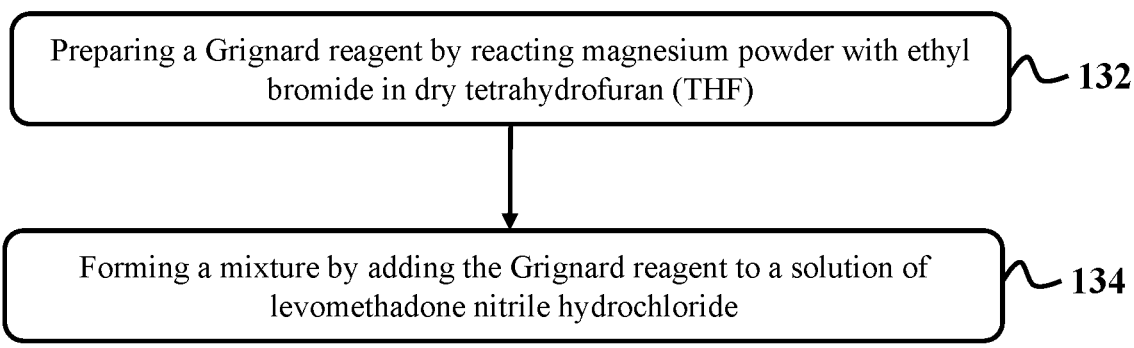
FIG. 1F illustrates an exemplary method for producing levomethadone hydrochloride by exposing levomethadone nitrile hydrochloride to a Grignard reagent, consistent with one or more exemplary embodiments of the present disclosure.
Figure 2E:
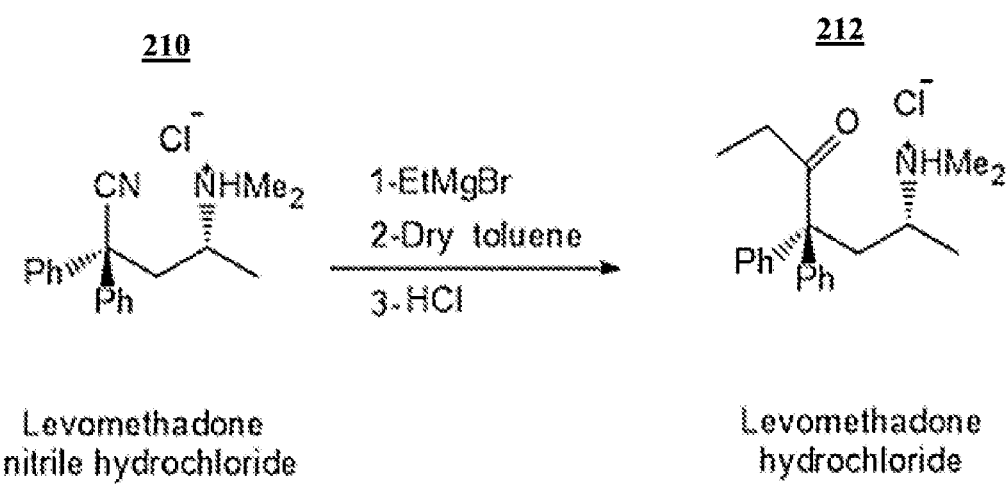
FIG. 2E illustrates a schematic representation for producing levomethadone hydrochloride, consistent with one or more exemplary embodiments of the present disclosure.

Referring back to FIG. 1A, in further detail with respect to step 110, in an exemplary embodiment, the exemplary method may include producing levomethadone hydrochloride by exposing the levomethadone nitrile hydrochloride to a Grignard reagent. FIG. 2E illustrates a schematic representation of step 110 for producing levomethadone hydrochloride 212. FIG. 1F illustrates an exemplary method for producing levomethadone hydrochloride 212 by exposing levomethadone nitrile hydrochloride 210 to the Grignard reagent, consistent with one or more exemplary embodiments of the present disclosure.

Referring to FIG. 1F, exposing levomethadone nitrile hydrochloride 210 to the Grignard reagent may include preparing the Grignard reagent by reacting magnesium (Mg) powder with ethyl bromide in dry tetrahydrofuran (THF) (step 132) and forming a mixture by adding the Grignard reagent to a solution of levomethadone nitrile hydrochloride 210 (step 134). In further detail with respect to step 132, in an exemplary embodiment, preparing the Grignard reagent by reacting Mg powder with ethyl bromide in THF may include refluxing the Mg and the ethyl bromide in dry THF for a time period of about five (5) hours under a nitrogen atmosphere. In an exemplary embodiment, reacting Mg powder with the ethyl bromide in THF may include reacting Mg powder with an amount of about 0.6171 mmoles with the ethyl bromide with an amount of about 0.1835 mmoles in 2 ml of dry THF. In an exemplary embodiment, refluxing Mg and ethyl bromide in dry THF may include mixing the Mg powder and ethyl bromide in dry THF with a weight ratio of about 3:4. In an exemplary embodiment, the Grignard reagent may include ethyl magnesium bromide.

In further detail with respect to step 134, in an exemplary embodiment, forming the mixture by adding the Grignard reagent to the solution of levomethadone nitrile hydrochloride 210 may include adding the Grignard solution the solution of levomethadone nitrile hydrochloride 210 through an additional funnel for a time period of about 15 minutes. In an exemplary embodiment, the solution of levomethadone nitrile hydrochloride 210 may have a concentration of about 0.04175 M in dry toluene. In an exemplary embodiment, forming the mixture by adding the Grignard reagent to the solution of levomethadone nitrile hydrochloride 210 may include adding the Grignard solution to the solution of levomethadone nitrile hydrochloride 210 with a temperature of about −15° C.

In an exemplary embodiment, the reaction mixture may be cooled to a temperature of about −15° C. utilizing an ice-salt-acetone bath. In an exemplary embodiment, exposing the levomethadone nitrile hydrochloride 210 to the Grignard reagent may further include distilling the THF out of the reaction mixture. In an exemplary embodiment, distilling the THF out of the reaction mixture may include warming the reaction mixture to room temperature and slowly heated to a temperature of about 70° C.

EXAMPLES

Example 1: Forming N,N-Dimethyl-D-Alanine

In this example, N,N-dimethyl-D-alanine was formed utilizing a process similar to step 102 of exemplary method 100 as presented in FIG. 1. At first, a solution of D-alanine had a concentration of 0.33 M with a pH level of 5.25 and was formed in a round bottom flask by dissolving 6 mmoles of D-alanine in 18 ml of deionized water. Then, formaldehyde 37% with an amount of about 24.3 mmoles was added to the solution of D-alanine to form a mixture. The mixture was stirred at room temperature for two (2) minutes. After that, sodium dihydrogen phosphate.$2H_2O$ with an amount of about 36.9 mmoles was added to the mixture and stirred at room temperature for 1 hour. Then, the round bottom flask was put in water bath with a temperature of about 20° C. and zinc dust with an amount of about 45 mmoles was added and stirred at room temperature for 1 hour.

Again, formaldehyde 37% with an amount of about 24.3 mmoles was added, followed by adding 18 ml deionized water, and then stirred at room temperature 2 minutes. Then, sodium dihydrogen phosphate.$2H_2O$ with an amount of about 36.9 mmoles was added and stirred at room temperature for 1 hour. After this time, zinc dust with an amount of about 45 mmoles was added and stirred at room temperature for 1 hour. This process was repeated twice to complete the reaction of forming N,N-dimethyl-D-alanine. The reaction progress was checked by thin-layer chromatography (TLC) using n-butanol, acetic acid, and water with a ratio of 2:1:1, respectively. The TLC was visualized using ninhydrin. The reaction was completed after 24 hours and the reaction mixture was filtered and the filtrate was adjusted to a pH level of about 7 by adding an ammonia solution while stirring at this pH level for a time period of about 45 minutes. Then, the filtrate was concentrated under reduced pressure to form a residue.

After that, methanol with an amount of about 100 ml was added to the residue and remained for fifteen (15) minutes. Then, the reaction mixture was mechanically stirred for one (1) hour and filtered. The filtrate was concentrated utilizing a rotary evaporator. Again, about 30 ml methanol was added to the residue and stirred for twenty (20) minutes and filtered using a filter paper. Then, the filtrate was concentrated by evaporating the solvent utilizing a rotary evaporator, leading to a crude product that recrystallized from hot ethanol/acetone. In the end, N,N-dimethyl-D-alanine with an amount of about 0.6466 gram and with a yield of about 92% was obtained.

Figure 3:
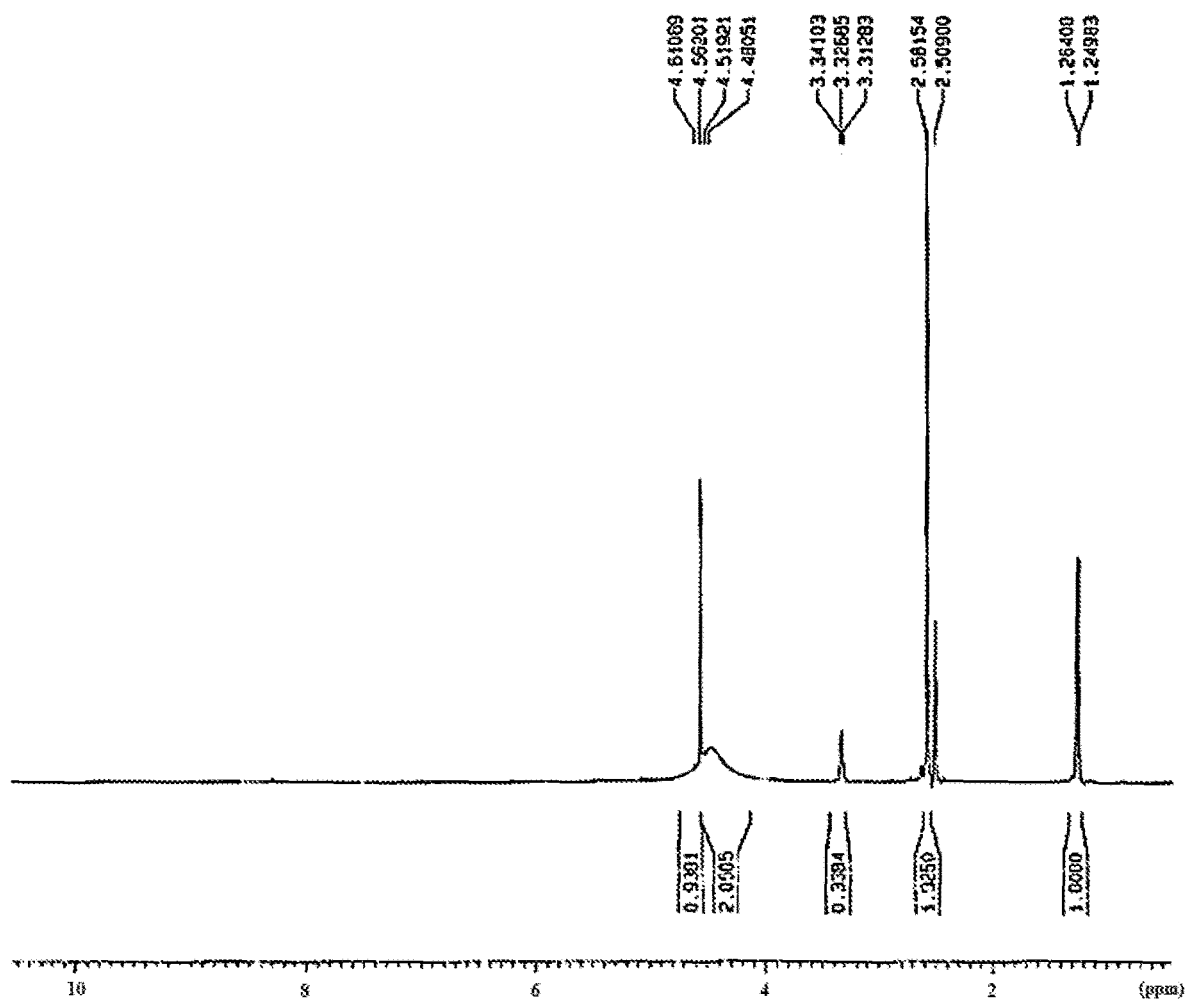
FIG. 3 illustrates a proton nuclear magnetic resonance ($^1$H NMR) spectrum of N, N-dimethyl D-alanine, consistent with one or more exemplary embodiments of the present disclosure.

The optical purity of N,N-dimethyl-D-alanine was confirmed by its optical rotation. FIG. 3 shows a proton nuclear magnetic resonance ($^1H$ NMR) spectrum of N,N-dimethyl-D-alanine, consistent with one or more exemplary embodiments of the present disclosure. Referring to FIG. 3, the $^1H$ NMR spectrum was consistent with the proposed structure of N,N-dimethyl-D-alanine. $[\alpha]25D=-10°$ (c=5, $H_2O$), Literature Data: $[\alpha]25D=-10.5°$ (c=5.12, $H_2O$), m.p=188° C., Literature Data: m.p=184° C., 1HNMR (500 MHZ, DMSO)=δ 1.24 (d, J=7.1 Hz, 3H), 2.58 (s, 6H), 3.31-3.34 (m, 1H), 4.48 (brs, 1H) ppm. Characteristic chemical shifts (δ) are given in parts-per-million using conventional abbreviations for designation of major peaks, such as s for singlet; d for doublet; t for triplet; q for a quartet; m for a multipet, and brs for broad singlet.

Figure 4:
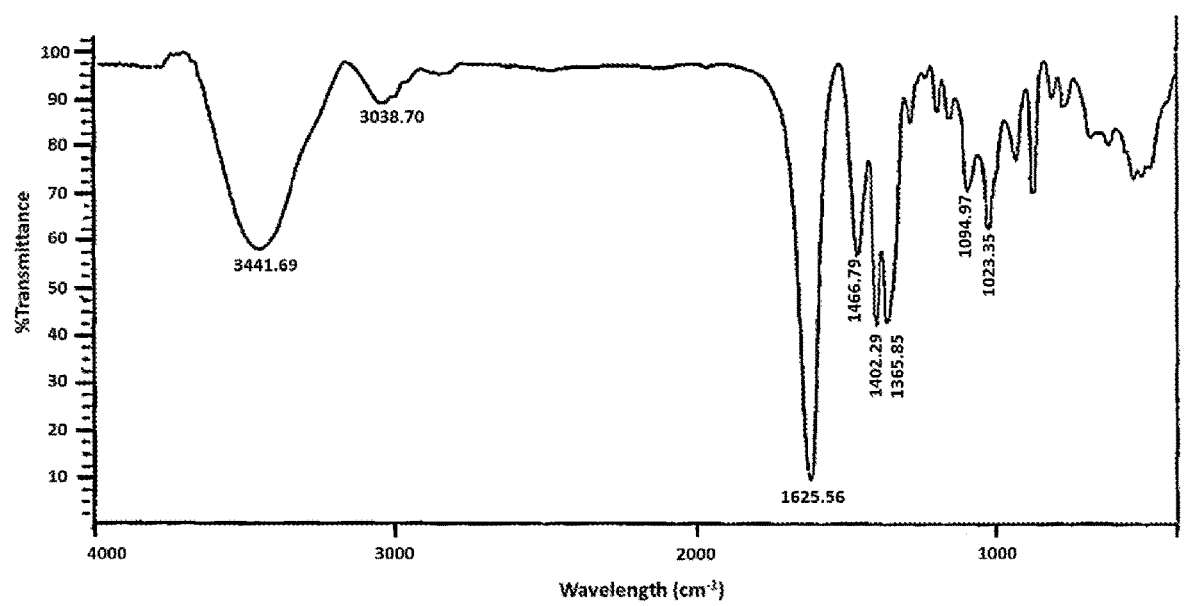
FIG. 4 illustrates a Fourier-transform infrared (FTIR) spectrum of N, N-dimethyl D-alanine, consistent with one or more exemplary embodiments of the present disclosure.

FIG. 4 shows a Fourier-transform infrared (FTIR) spectrum of N,N-dimethyl-D-alanine, consistent with one or more exemplary embodiments of the present disclosure. Referring to FIG. 4, spectrum of N,N-dimethyl-D-alanine exhibited peaks at wavelengths 3441 $cm^{-1}$, 3038 $cm^{-1}$, 1625 $cm^{-1}$, 1466 $cm^{-1}$, 1402 $cm^{-1}$, 1365 $cm^{-1}$, 1094 $cm^{-1}$, 1023 cm' which may be attributed to the structure of N,N-dimethyl-D-alanine.

Example 2: Producing (R)-2-(Dimethylamino) Propan-1-Ol

In this example, (R)-2-(dimethylamino) propan-1-ol was produced utilizing a process similar to step 104 of exemplary method 100 as presented in FIG. 1. At first, a solution of N,N-dimethyl-D-alanine had a concentration of about 0.57 M with a pH level of about 7.28 and was prepared by dissolving about 0.8536 mmoles of N,N-dimethyl-D-alanine in 1.5 ml of deionized water. Then, a reaction mixture was formed by adding nickel chloride ($NiCl_2.6H_2O$) as a complexing agent with an amount of about 2.9022 mmoles to the solution of N,N-dimethyl-D-alanine. The reaction mixture was stirred at room temperature for 2 hours. Again, $NiCl_2.6H_2O$ with an amount of about 0.5099 mmoles was added to the reaction mixture and stirred at room temperature for one (1) hour.

After that, the reaction mixture was added to a separated flask that contained 200 ml deionized water with a pH level of 7.28 and stirred for three (3) minutes. Then borax.$10H_2O$ with an amount of about 27.3150 mmoles was added to the reaction mixture and stirred at room temperature to chemically reduce the N,N-dimethyl-D-alanine to (R)-2-(dimethylamino) propan-1-ol. After 3 hours, about 45 ml of deionized water was added for two times with an interval of about 15 minutes. The reaction mixture was stirred for 2.5 days at a temperature of about 25° C. The reaction progress was also checked utilizing thin-layer chromatography (TLC) using a solution including n-hexane, ethyl acetate, and methanol with a ratio of about 1:1:1.

After that, the pH of the reaction mixture was adjusted to a pH level of about 12.5 by adding a solution of KOH with a concentration of 60% and stirred at this pH level for one (1) hour. The pH level was checked and the reaction mixture was saturated with NaCl and extracted with chloroform. The aqueous phase was divided into three (3) portions with a volume of about 100 ml and each portion was extracted using 140 ml chloroform (7*20 ml). The organic phase of extracts was evaporated at room temperature slowly. After concentration, the (R)-2-(dimethylamino) propane-1-ol was dried using anhydrous $MgSO_4$. Then, dried (R)-2-(dimethylamino) propane-1-ol was purified by thick layer chromatography using a solution including n-hexane, ethyl acetate, and methanol. In the end, the yield of the reaction was about 41% and about 0.0361 gram of (R)-2-(dimethylamino) propane-1-ol (3) was obtained as a volatile oil.

Figure 5:
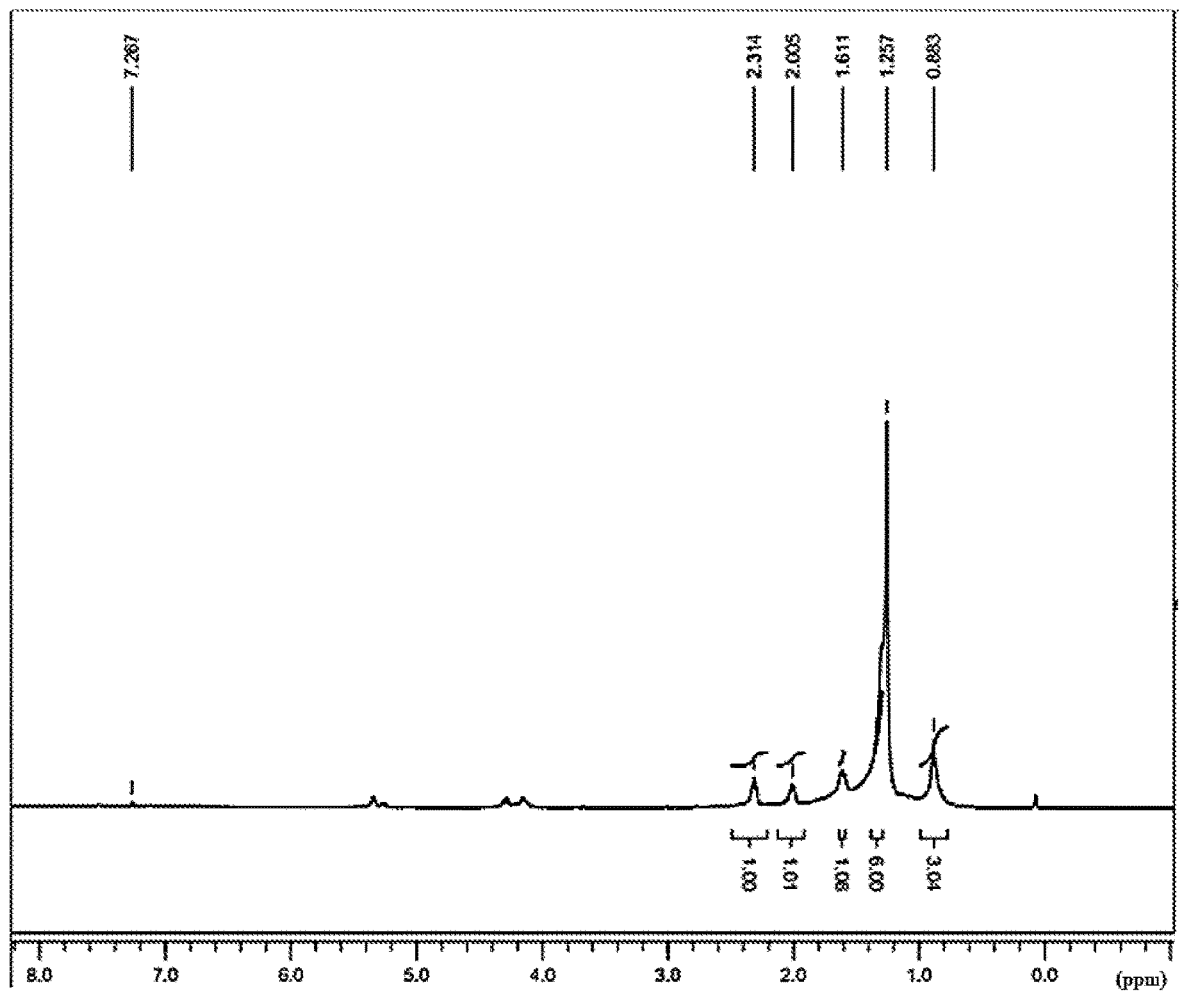
FIG. 5 illustrates a $^1$H NMR spectrum of (R)-2-(dimethylamino) propane-1-ol, consistent with one or more exemplary embodiments of the present disclosure.

The optical purity of (R)-2-(dimethylamino) propane-1-ol was confirmed by its optical rotation. FIG. 5 shows a $^1H$ NMR spectrum of (R)-2-(dimethylamino) propane-1-ol, consistent with one or more exemplary embodiments of the present disclosure. Referring to FIG. 5, the $^1H$ NMR spectrum was consistent with the proposed structure of (R)-2-(dimethylamino) propane-1-ol. $[\alpha]25D=-3.80°$ (c=2.8, EtOH), Literature Data: $[\alpha]25D=-3.83°$ (c=2.9, EtOH), 1HNMR (400 MHZ, CDCl3)=δ 0.88 (m, 3H), 1.25 (s, 6H), 1.61 (m, 1H), 2.0 (m, 1H), 2.3 (m, 1H) ppm.

Figure 6:
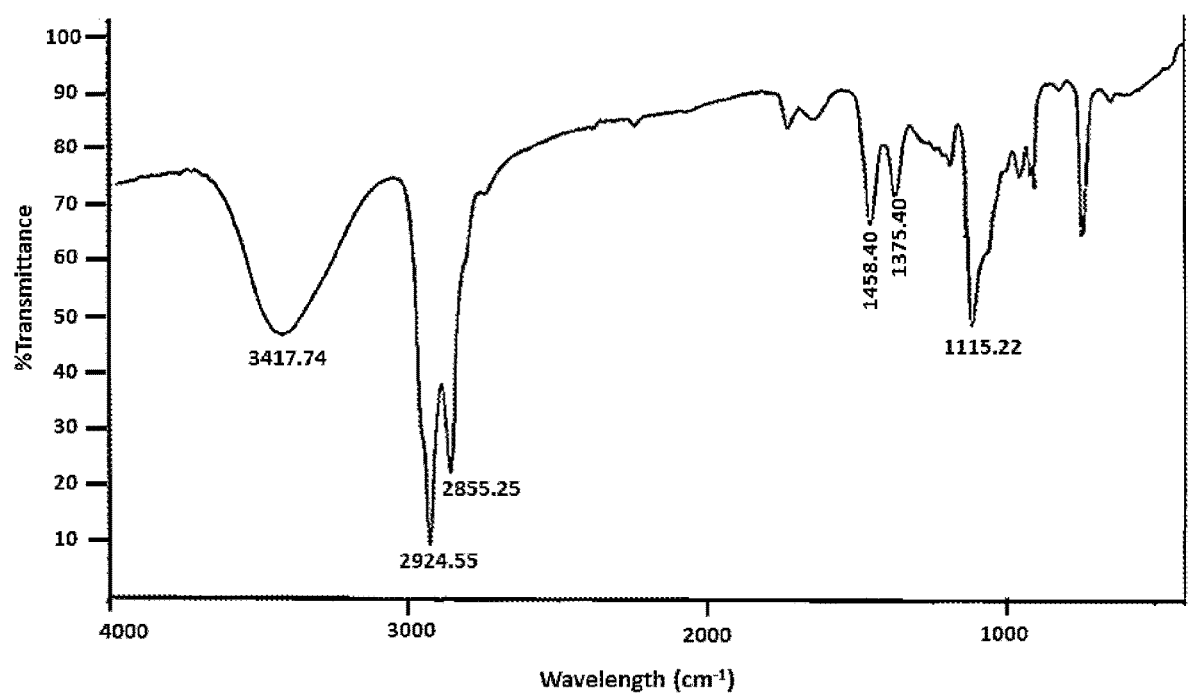
FIG. 6 illustrates an FTIR spectrum of (R)-2-(dimethylamino) propane-1-ol, consistent with one or more exemplary embodiments of the present disclosure.
Figure 7:
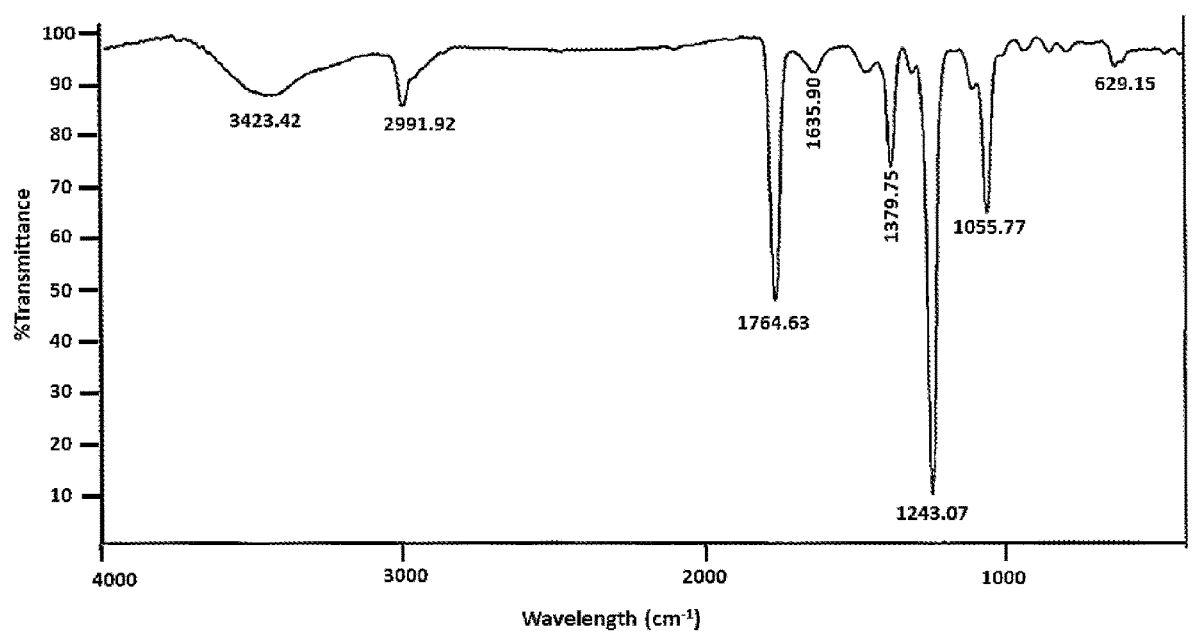
FIG. 7 illustrates an FTIR spectrum of ethyl acetate, consistent with one or more exemplary embodiments of the present disclosure.

FIG. 6 shows an FTIR spectrum of (R)-2-(dimethylamino) propane-1-ol, consistent with one or more exemplary embodiments of the present disclosure. FIG. 7 shows an FTIR spectrum of ethyl acetate as a control group, consistent with one or more exemplary embodiments of the present disclosure. Referring to FIGS. 6 and 7, spectrum of (R)-2-(dimethylamino) propane-1-ol exhibited peaks at wavelengths $3417\ cm^{-1}$, $2924\ cm^{-1}$, $2855\ cm^{-1}$, $1458\ cm^{-1}$, $1375\ cm^{-1}$, $1115\ cm^{-1}$ which may be attributed to the structure of (R)-2-(dimethylamino) propane-1-ol.

Figure 8:
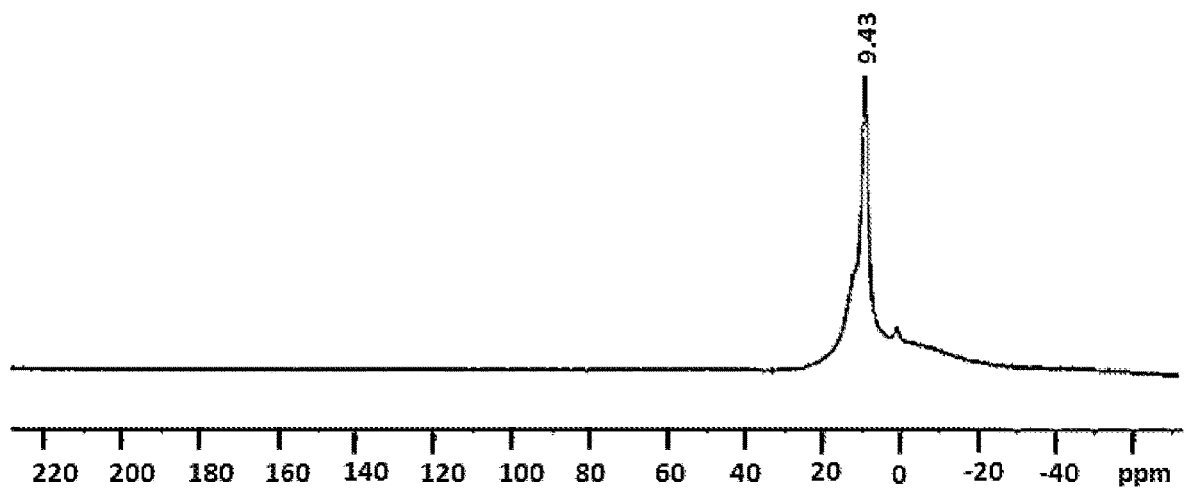
FIG. 8 illustrates a boron nuclear magnetic resonance ($^{11}$B NMR) spectrum of pure borax, consistent with one or more exemplary embodiments of the present disclosure.

In this step, borax, N,N-dimethyl-D-alanine, and $NiCl_2.6H_2O$ were complexed with each other in water to form (R)-2-(dimethylamino) propane-1-ol. In order to monitor the complexation between the borax, the N,N-dimethyl-D-alanine, and the $NiCl_2.6H_2O$ boron nuclear magnetic resonance ($^{11}B$ NMR) spectra were taken in different situations from the reaction mixture. At first, the $^{11}B$ NMR spectrum was taken from the mixture that contains only borax without N,N-dimethyl-D-alanine and the $NiCl_2.6H_2O$ in water after 48 hours. FIG. 8 shows an $^{11}B$ NMR spectrum of pure borax, consistent with one or more exemplary embodiments of the present disclosure. Referring to FIG. 8, the $^{11}B$ NMR spectrum of pure borax exhibited a singlet band at 9.43 ppm.

Figure 9:
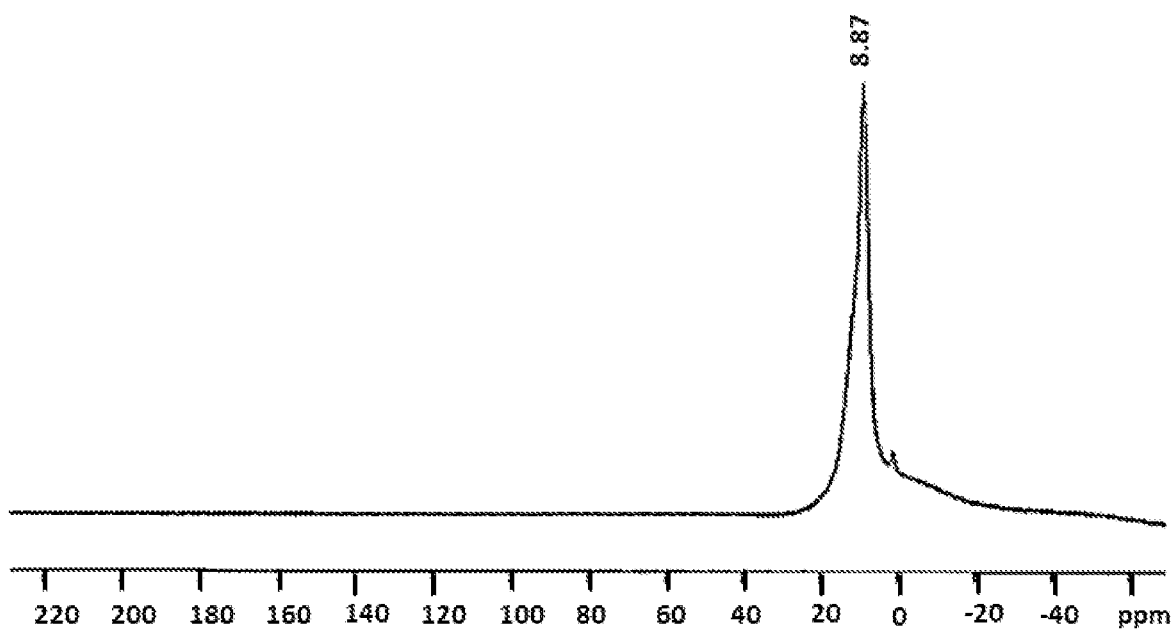
FIG. 9 illustrates an $^{11}$B NMR spectrum of a reaction mixture after complexation of borax with N,N-dimethyl-D-alanine and $NiCl_2.6H_2O$, consistent with one or more exemplary embodiments of the present disclosure.

Again, the $^{11}B$ NMR spectrum was taken from the mixture that contained borax with N,N-dimethyl-D-alanine and $NiCl_2.6H_2O$ in water after 48 hours before adjustment of the pH level. FIG. 9 shows an $^{11}B$ NMR spectrum of the reaction mixture after complexation of borax with N,N-dimethyl-D-alanine and $NiCl_2.6H_2O$, consistent with one or more exemplary embodiments of the present disclosure. Referring to FIG. 9, the spectrum of the reaction mixture showed a singlet band at 8.87 ppm. The shift in the singlet band indicates that complexation occurred between borax, N,N-dimethyl-D-alanine, and $NiCl_2.6H_2O$ in water and also reduction reaction was carried out probably on the surface of borax.

Figure 10:
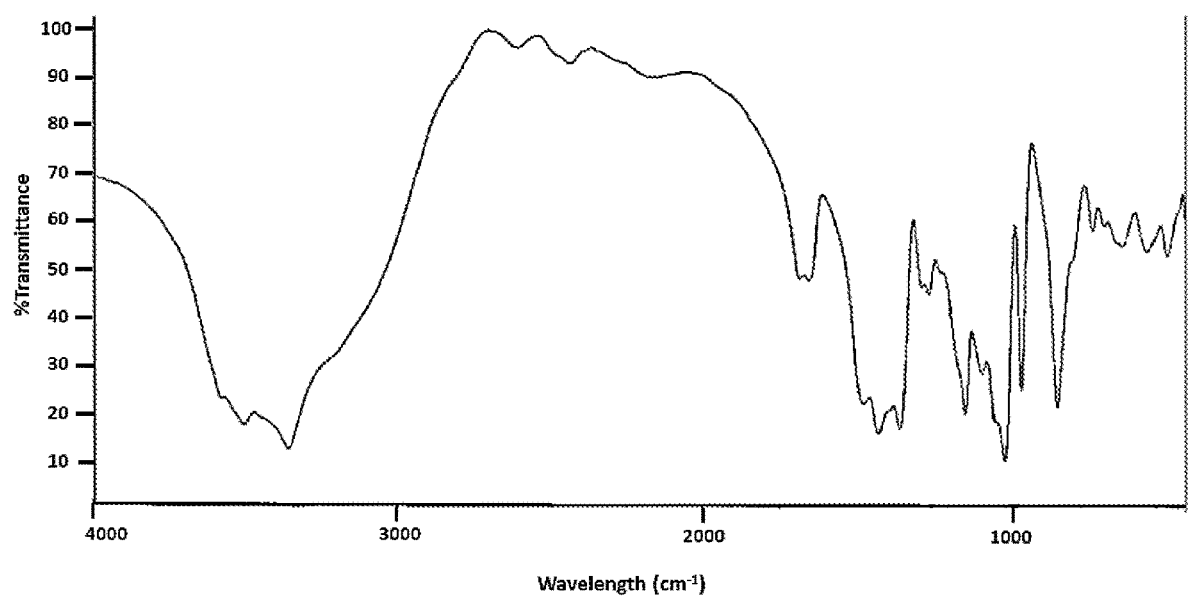
FIG. 10 illustrates an FTIR spectrum of pure borax, consistent with one or more exemplary embodiments of the present disclosure.
Figure 11:
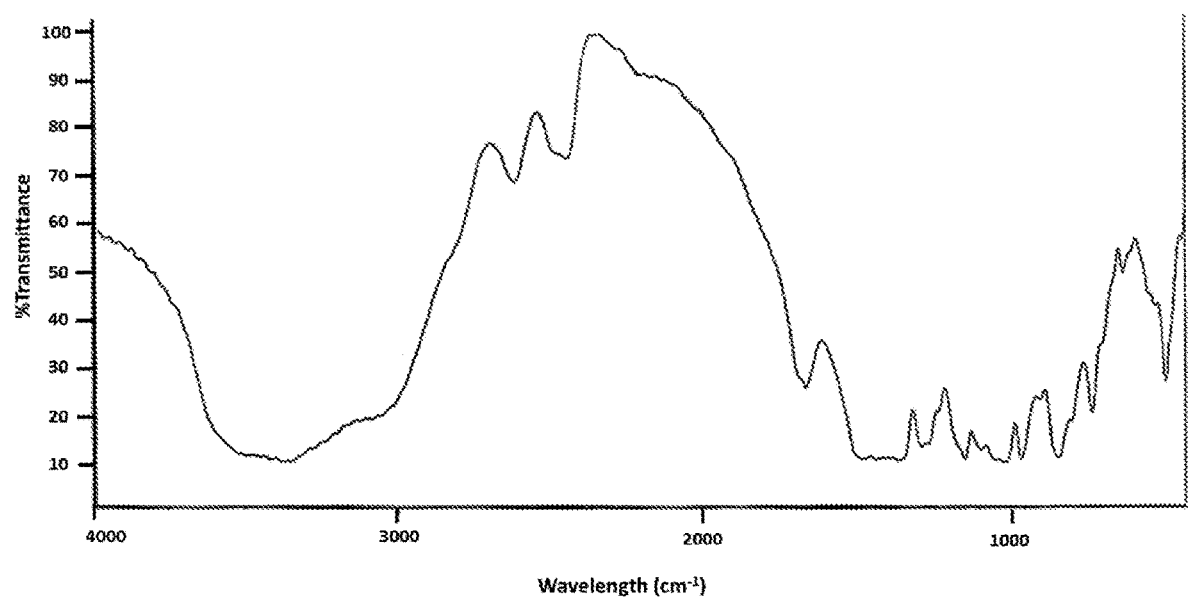
FIG. 11 illustrates an FTIR spectrum of a reaction mixture after 20 hours, consistent with one or more exemplary embodiments of the present disclosure.
Figure 12:
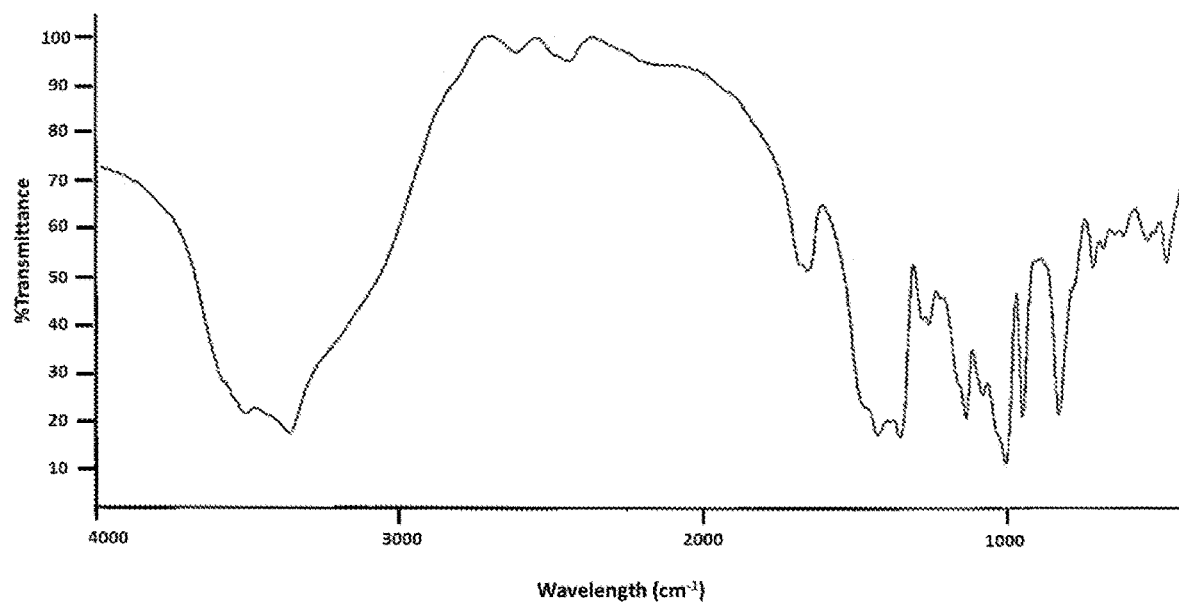
FIG. 12 illustrates an FTIR spectrum of a reaction mixture before pH adjustment, consistent with one or more exemplary embodiments of the present disclosure.

Moreover, complexation between the borax, the N,N-dimethyl-D-alanine, and $NiCl_2.6H_2O$ was also proved using FTIR analysis. FIG. 10 shows an FTIR spectrum of pure borax, consistent with one or more exemplary embodiments of the present disclosure. FIG. 11 shows an FTIR spectrum of the reaction mixture containing borax, N,N-dimethyl-D-alanine, and $NiCl_2.6H_2O$ after 20 hours, consistent with one or more exemplary embodiments of the present disclosure. FIG. 12 shows an FTIR spectrum of the reaction mixture containing borax, N,N-dimethyl-D-alanine, and $NiCl_2.6H_2O$ before pH adjustment, consistent with one or more exemplary embodiments of the present disclosure.

Figure 13:
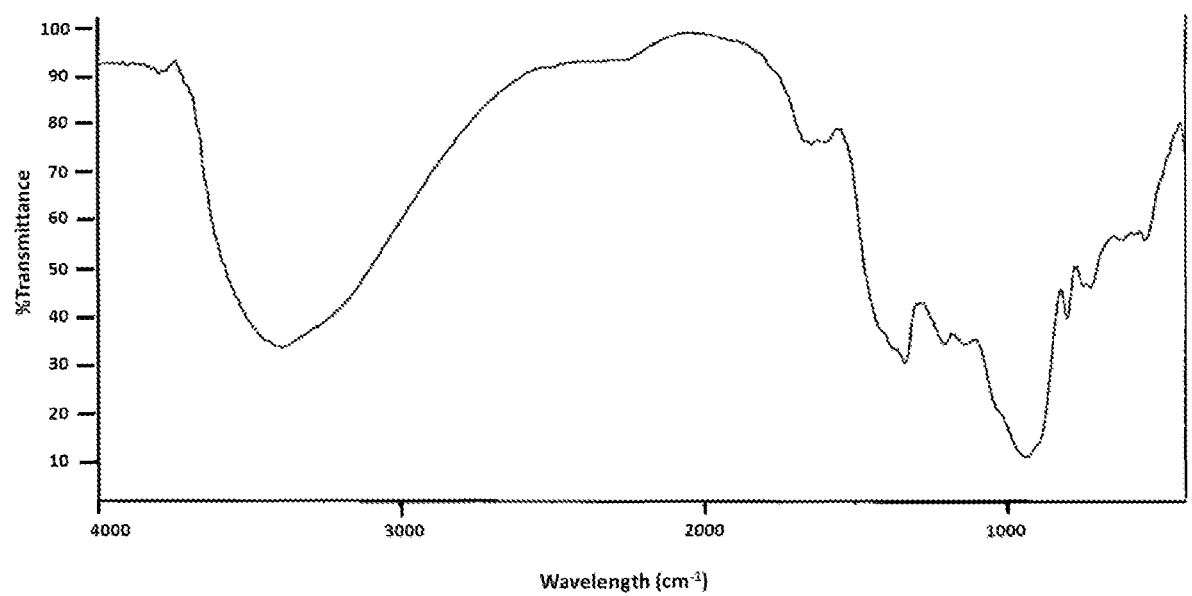
FIG. 13 illustrates an FTIR spectrum of a reaction mixture after pH adjustment, consistent with one or more exemplary embodiments of the present disclosure.

FIG. 13 shows an FTIR spectrum of the reaction mixture containing borax, N,N-dimethyl-D-alanine, and $NiCl_2.6H_2O$ after pH adjustment to the pH level of 12.5, consistent with one or more exemplary embodiments of the present disclosure. Referring to FIGS. 10-13, different FTIR spectra are observed from a reaction mixture in different situations and times which indicates the progress in the complexation between the borax, the N,N-dimethyl-D-alanine, and the $NiCl_2.6H_2O$.

Figure 14:
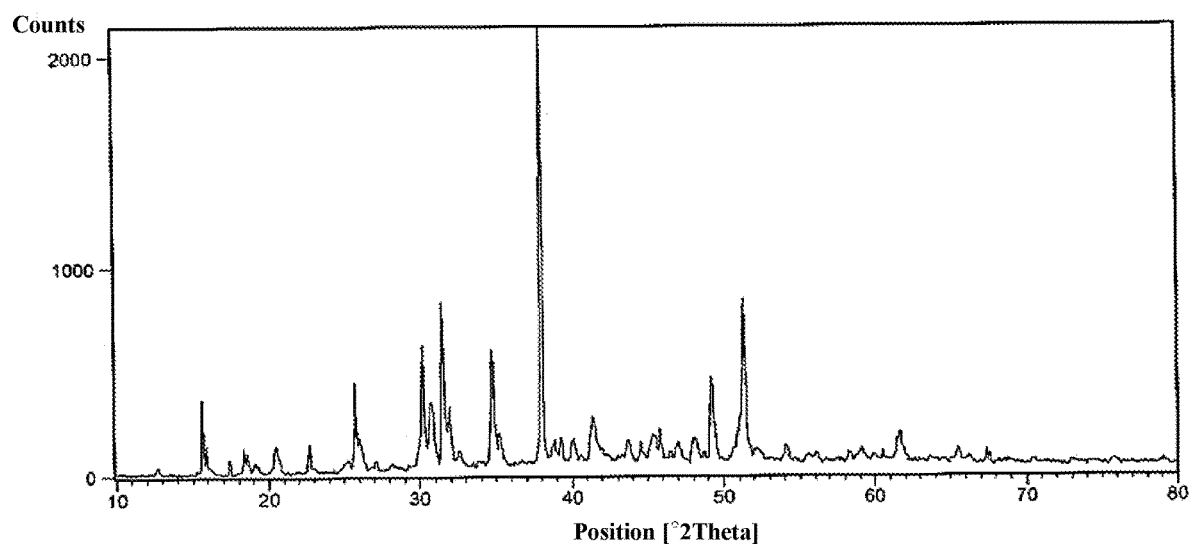
FIG. 14 illustrates an X-ray powder diffraction (XRD) pattern of pure borax, consistent with one or more exemplary embodiments of the present disclosure.
Figure 15:
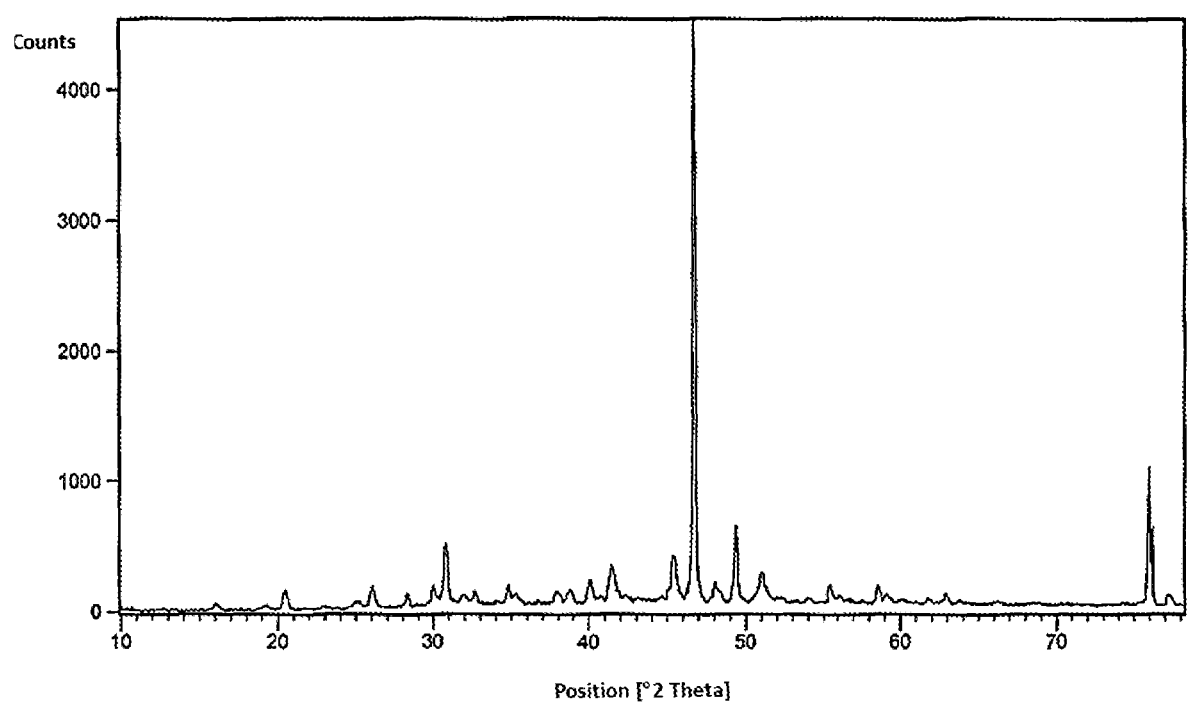
FIG. 15 illustrates an XRD pattern of a reaction mixture after 20 hours, consistent with one or more exemplary embodiments of the present disclosure.
Figure 16:
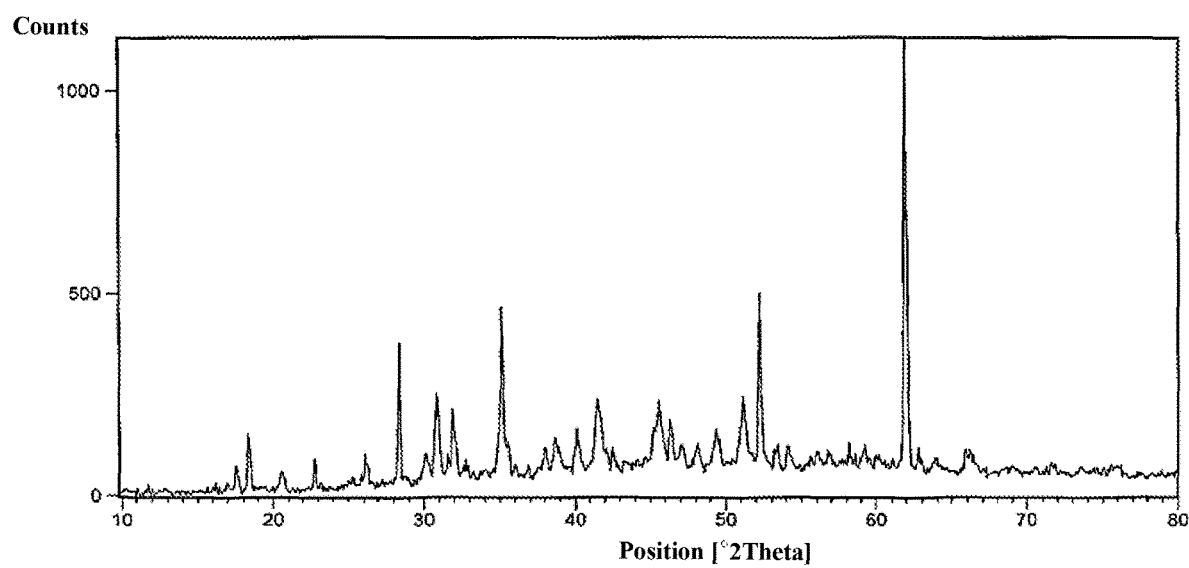
FIG. 16 illustrates an XRD pattern of a reaction mixture before pH adjustment, consistent with one or more exemplary embodiments of the present disclosure.

Furthermore, complexation between the borax, the N,N-dimethyl-D-alanine, and $NiCl_2.6H_2O$ was also examined using X-ray powder diffraction (XRD) analysis. FIG. 14 shows an XRD pattern of pure borax, consistent with one or more exemplary embodiments of the present disclosure. FIG. 15 shows an XRD pattern of the reaction mixture containing the borax, the N,N-dimethyl-D-alanine, and the $NiCl_2.6H_2O$ after 20 hours, consistent with one or more exemplary embodiments of the present disclosure. FIG. 16 shows an XRD pattern of the reaction mixture containing the borax, the N,N-dimethyl-D-alanine, and $NiCl_2.6H_2O$ before pH adjustment, consistent with one or more exemplary embodiments of the present disclosure.

Figure 17:
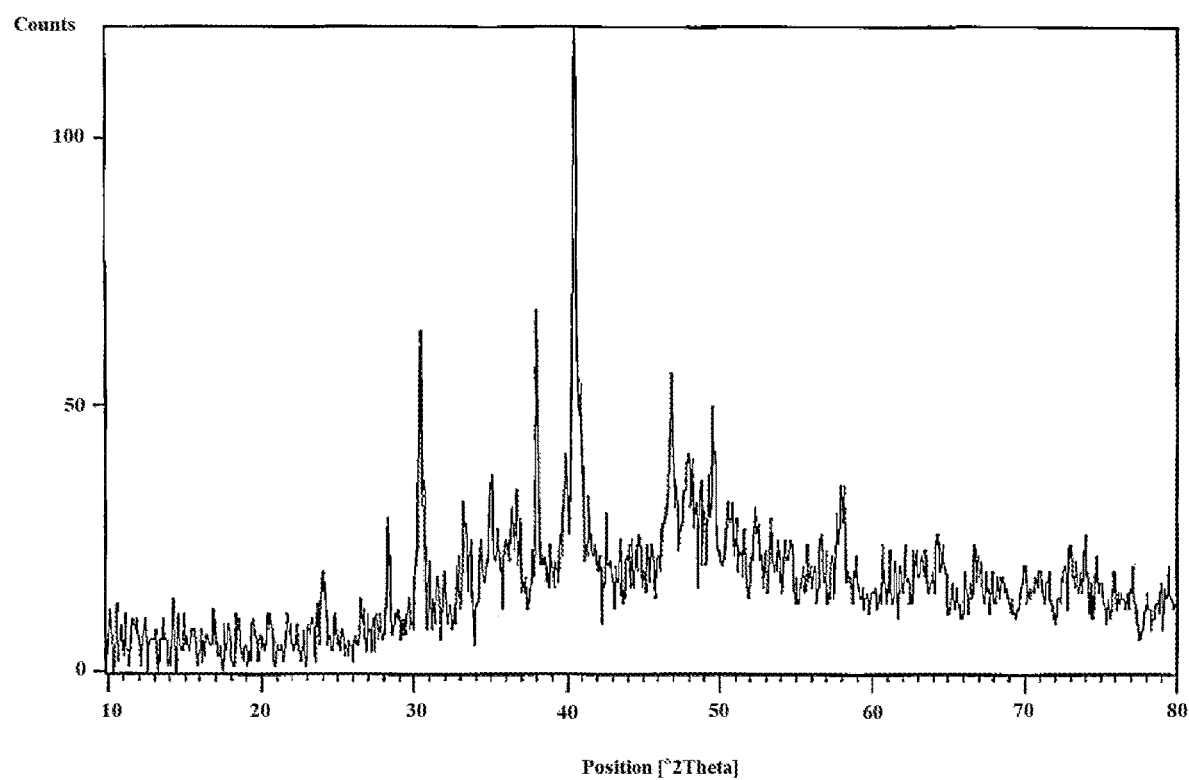
FIG. 17 illustrates an XRD pattern of a reaction mixture after pH adjustment, consistent with one or more exemplary embodiments of the present disclosure.

FIG. 17 shows an XRD pattern of the reaction mixture containing the borax, the N,N-dimethyl-D-alanine, and the $NiCl_2.6H_2O$ after pH adjustment, consistent with one or more exemplary embodiments of the present disclosure. Referring to FIGS. 14-17, different XRD patterns are observed from the reaction mixture in different situations and times which indicates the progress in the complexation between the borax, the N,N-dimethyl-D-alanine, and the $NiCl_2.6H_2O$.

Example 3: Forming
(R)-1-Chloro-N,N-Dimethylpropane-2-Amine
Hydrochloride

In this example, (R)-1-chloro-N,N-dimethylpropane-2-amine hydrochloride was formed utilizing a process similar to step 106 of the exemplary method 100 as presented in FIG. 1. At first, 25 ml HCl with a concentration of about 37% was dropwise added to (R)-2-(dimethylamino) propane-1-ol with an amount of about 0.155 mmol (0.016 g) at room temperature over a period of three (3) hours. The reaction mixture was allowed to stir for an additional five (5) hours. Then, the excess amount of HCl of the reaction mixture was slowly evaporated using the air flow under a hood, and (R)-2-(dimethylamino) propan-1-ol with HCl trapped was obtained as a yellow oil.

Figure 18:
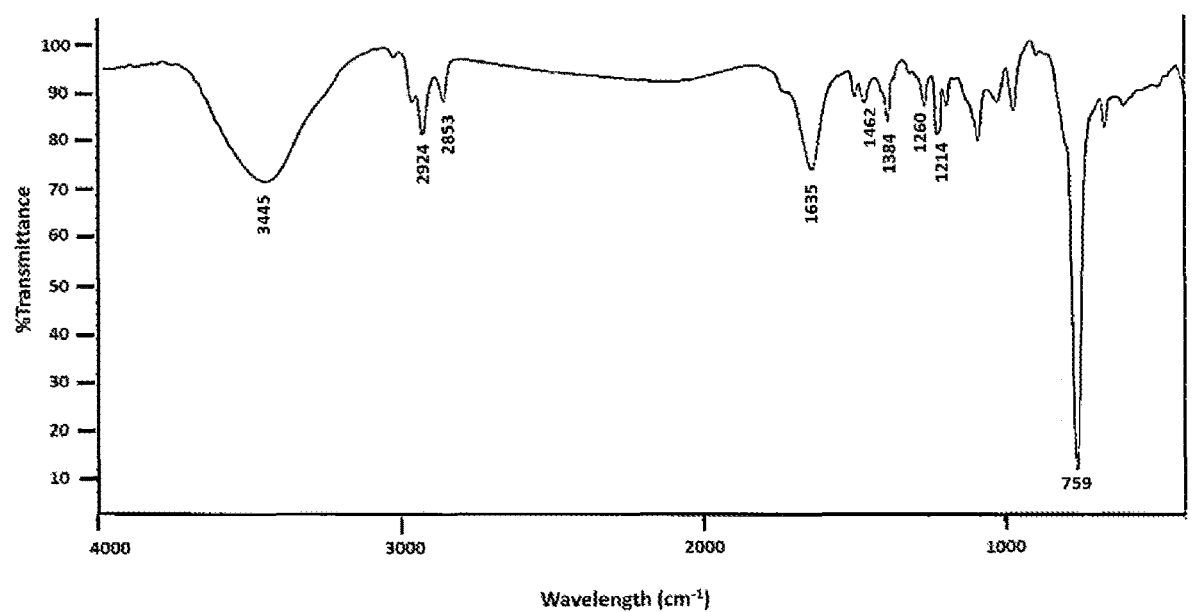
FIG. 18 illustrates an FTIR spectrum of (R)-2-(dimethylamino) propane-1-ol with HCl trapped, consistent with one or more exemplary embodiments of the present disclosure.

FIG. 18 shows an FTIR spectrum of (R)-2-(dimethylamino) propane-1-ol with HCl trapped, consistent with one or more exemplary embodiments of the present disclosure.

Referring to FIG. 18, spectrum of (R)-2-(dimethylamino) propane-1-ol with HCl trapped exhibited peaks at wavelengths 3445 cm$^{-1}$, 2924 cm$^{-1}$, 2853 cm$^{-1}$, 1635 cm$^{-1}$, 1462 cm$^{-1}$, 1384 cm$^{-1}$, 1260 cm$^{-1}$, 1214 cm$^{-1}$, 759 cm$^{-1}$ which may be attributed to the structure of (R)-2-(dimethylamino) propane-1-ol with HCl trapped.

After that, the yellow oil as the (R)-2-(dimethylamino) propane-1-ol with HCl trapped was dissolved in about 0.6 ml dry chloroform under heating at a temperature of about 50° C. using a heater stirrer. The obtained solution was added dropwise to a solution of thionyl chloride in dry chloroform with a volume ratio of (thionyl chloride:chloroform) about 7:8 at room temperature over 45 minutes under a nitrogen atmosphere. It should be noted that addition of the (R)-2-(dimethylamino) propane-1-ol with HCl trapped to the solution of thionyl chloride is classified as a reaction with inverse addition which obviates the need for performing the reaction in an ice-bath. The reaction mixture was allowed to stir for an additional 5 hours at room temperature until a white precipitate was formed. After concentration, the reaction mixture was cooled and diluted with diethyl ether. In this process, about 0.020 gram of (R)-1-chloro-N, N-dimethylpropane-2-amine hydrochloride was obtained with a yield of about 83%.

Figure 19:
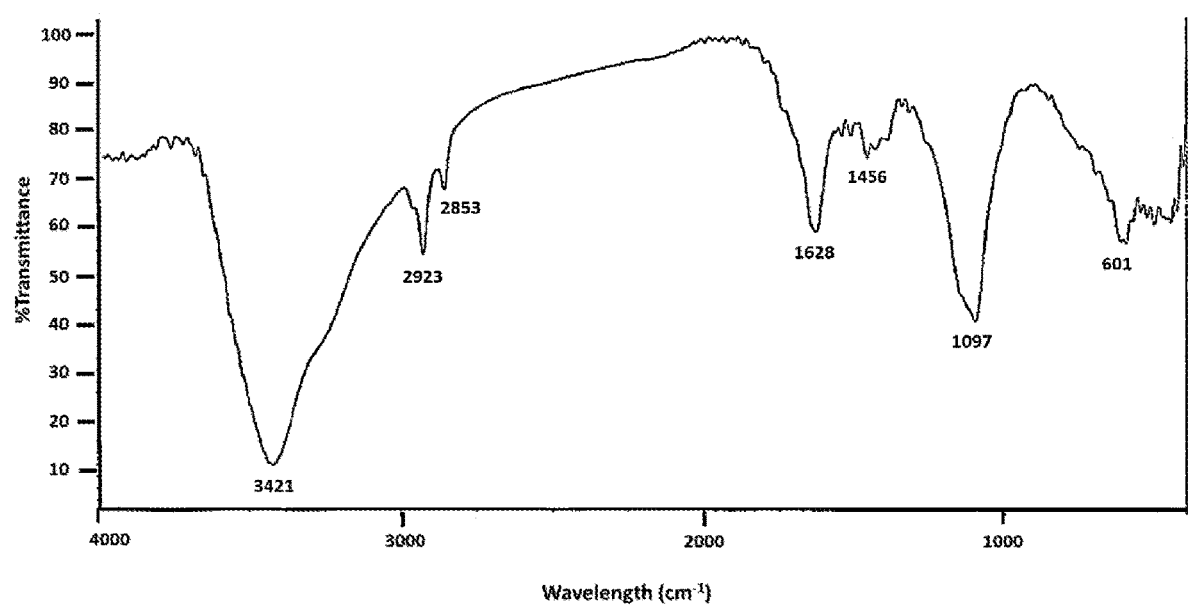
FIG. 19 illustrates an FTIR spectrum of (R)-1-chloro-N,N-dimethylpropane-2-amine hydrochloride, consistent with one or more exemplary embodiments of the present disclosure.

FIG. 19 shows an FTIR spectrum of (R)-1-chloro-N,N-dimethylpropane-2-amine hydrochloride, consistent with one or more exemplary embodiments of the present disclosure. Referring to FIG. 19, spectrum of (R)-1-chloro-N,N-dimethylpropane-2-amine hydrochloride exhibited peaks at wavelengths 3421 cm$^{-1}$, 2923 cm$^{-1}$, 2853 cm$^{-1}$, 1628 cm$^{-1}$, 1456 cm$^{-1}$, 1097 cm$^{-1}$, and 601 cm$^{-1}$ which may be attributed to the structure of (R)-1-chloro-N,N-dimethylpropane-2-amine hydrochloride.

Example 4: Synthesis of Levomethadone Nitrile Hydrochloride

In this example, levomethadone nitrile hydrochloride was synthesized utilizing a process similar to step 108 of the exemplary method 100 as presented in FIG. 1. At first, diphenylacetonitrile with an amount of about 0.08176 mmoles was added to a stirred suspension of (R)-1-chloro-N, N-dimethylpropane-2-amine hydrochloride (0.0316 mmoles, 0.005 g) in dry DMF (0.5 ml) at room temperature under a nitrogen atmosphere. The resulting mixture was stirred for 5 minutes and then cooled to 0° C. utilizing an ice-salt bath. After that, potassium t-butoxide with an amount of about 0.1248 mmoles was added slowly and the mixture was stirred vigorously at a temperature of about 0° C. for 45 minutes to generate a yellow solution. Then, dry DMF (2 ml) was added to the reaction mixture.

The resulting mixture was warmed up to room temperature (RT) and heated utilizing an oil bath up to a temperature of 58° C. for 14 hours. During cooling the reaction mixture to ambient temperature, water (10 ml) was added to the reaction mixture and stirred for 30 minutes. Finally, the aqueous phase was saturated with NaCl and then extracted using 75 ml ethyl acetate. The combined organic extracts were dried over anhydrous sodium sulfate. After removal of the solvent, the residue was dissolved in 3 ml of heptane at a temperature of 80° C. and kept at room temperature overnight. The crude product was obtained as a white solid.

In this step, yellow oil, which indicates the presence of an undesirable isomer, did not appear. The crude product was purified by column chromatography on silica gel using a solution including n-hexane and ethyl acetate with a ratio of about 9:1. In the end, only desirable isomer of levomethadone nitrile hydrochloride with an amount of about 0.00846 gram was produced with a yield of about 85%.

Figure 20:
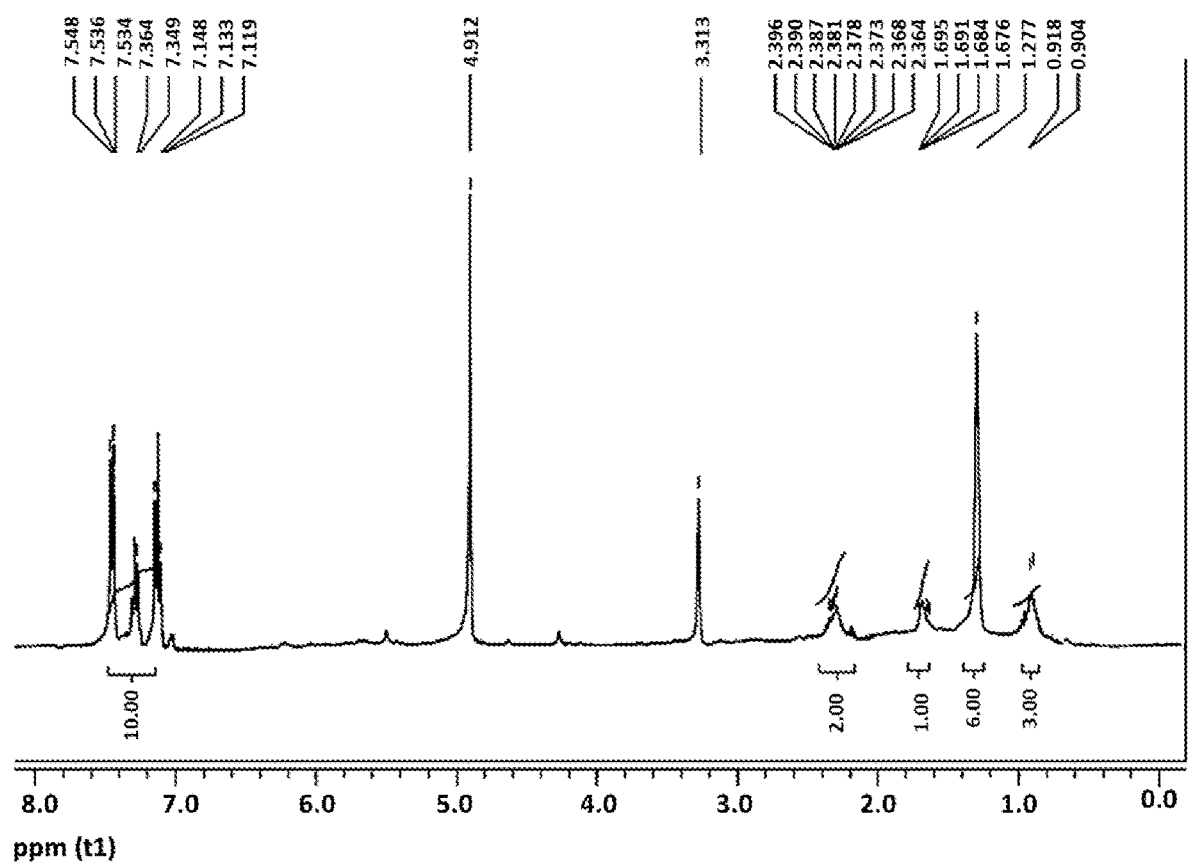
FIG. 20 illustrates a $^1$H NMR spectrum of levomethadone nitrile hydrochloride, consistent with one or more exemplary embodiments of the present disclosure.

The optical purity of levomethadone nitrile hydrochloride was confirmed by its optical rotation. FIG. 20 shows a $^1$H NMR spectrum of levomethadone nitrile hydrochloride, consistent with one or more exemplary embodiments of the present disclosure. Referring to FIG. 20, the $^1$H NMR spectrum was consistent with the proposed structure of levomethadone nitrile hydrochloride. $[\alpha]25D=-3.7°$ (c=4%, EtOH), Literature Data=-3.8° (c=5%, EtOH), m.p=210° C., Literature Data: m.p=211-212° C., $^1$H NMR (500 MHz. CD$_3$OD)/δ ppm: 0.90 (d, J=7.0 Hz, 3H), 1.27 (s, 6H), 1.68-1.69 (m, 1H), 2.36-2.39 (m, 2H), 7.12-7.54 (m, 10H) ppm.

Figure 21:
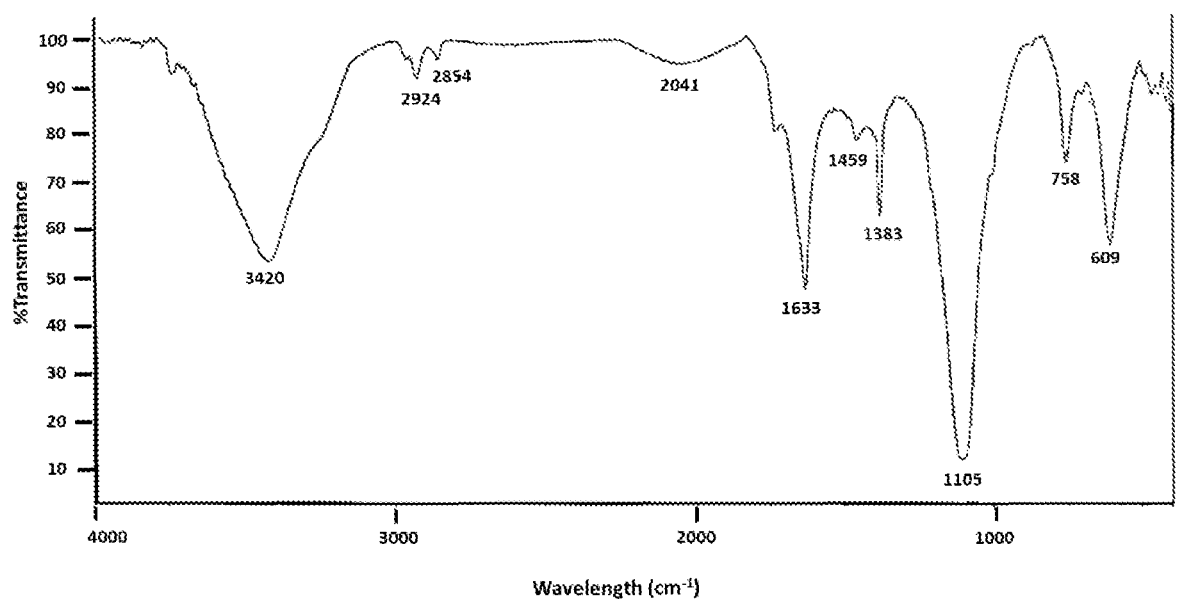
FIG. 21 illustrates an FTIR spectrum of levomethadone nitrile hydrochloride, consistent with one or more exemplary embodiments of the present disclosure.

FIG. 21 shows an FTIR spectrum of levomethadone nitrile hydrochloride, consistent with one or more exemplary embodiments of the present disclosure. Referring to FIG. 21, spectrum of levomethadone nitrile hydrochloride exhibited peaks at wavelengths 3420 cm$^{-1}$, 2924 cm$^{-1}$, 2854 cm$^{-1}$, 2041 cm$^{-1}$, 1633 cm$^{-1}$, 1459 cm$^{-1}$, 1383 cm$^{-1}$, 1105 cm$^{-1}$, 758 cm$^{-1}$, 609 cm$^{-1}$ which may be attributed to the structure of levomethadone nitrile hydrochloride. Also, the broad and sharp peak at a wavelength of about 3420 cm$^{-1}$ in the FTIR spectrum may be attributed to the N—H stretching of the levomethadone nitrile hydrochloride.

Also, ion chromatography technique was used for confirming the formation of levomethadone nitrile hydrochloride salt by examining the presence and measuring the amount of chloride ion. Therefore, it was shown that a sample of levomethadone nitrile hydrochloride salt synthesized in this example contains chloride ion with an amount of about 6.432 ppm.

Furthermore, silver nitrate experiments were performed to confirm the presence of chloride ion and formation of the levomethadone nitrile hydrochloride salt. At first, four following tubes were used: Tubes A and B contained solution of levomethadone nitrile hydrochloride salt in deionized water which were completely clear, Tube C contained only deionized water as a negative control, and Tube D contained drinking water as a positive control.

In the next step of silver nitrate experiments, a solution of silver nitrate with a concentration of about 1M was added slowly to all of the test tubes with shaking. As a result, tubes A, B, and D became opaque which represent the formation of AgCl in these tubes. Then, ammonia 25% was added slowly to all of the tubes, and tubes A, B, and D started to become clear from above of solution of each tube that represent the formation of Ag (NH$_3$)$_2$Cl complex and presence of chloride ion in these tubes. Therefore, these experiments confirmed the formation of levomethadone nitrile hydrochloride salt.

Example 5: Synthesis of Levomethadone Hydrochloride

In this example, levomethadone hydrochloride was synthesized utilizing a process similar to step 110 of the exemplary method 100 as presented in FIG. 1. At first, a solution of levomethadone nitrile hydrochloride was prepared by dissolving about 0.0835 mmoles (0.0263 g) of levomethadone nitrile hydrochloride in 2 ml of dry toluene under a nitrogen atmosphere. Then, ethyl magnesium bromide as a Grignard reagent was prepared by refluxing powder Mg with an amount of about 0.015 g and ethyl bromide with an amount of about 0.02 g in dry THF with an amount of about 2 ml for 5 hours.

After that, the reaction mixture was cooled to a temperature of about −15° C. utilizing an ice-salt-acetone bath and then ethyl magnesium bromide was added dropwise through an additional funnel for a time period of about fifteen (15) minutes. Also, a condenser was arranged for the distillation of the THF. The ice bath was removed and the reaction mixture warmed to RT and slowly heated to 60° C. and then 70° C. until the THF was distilled off. Then, the reaction mixture was heated to reflux for 5 hours utilizing an oil bath with a temperature of about 110° C. After being cooled to a temperature of about 0° C. utilizing an ice-salt bath, the nitrogen atmosphere was removed.

After that, the reaction was carefully quenched by dropwise adding about 0.1 ml water followed by adding 5 ml of HCl with a concentration of 6M under cooling utilizing an ice-salt bath. In order to remove an imine intermediate which was produced in this reaction, the reaction mixture was gradually heated up to a temperature of about 70° C. and stirred for 3 hours at this temperature to ensure the complete hydrolysis of the imine intermediate. Then, the reaction mixture was cooled to ambient temperature and adjusted to a pH level of about 12.5 by adding NaOH (0.74 g) in water (2 ml) under cooling with an ice-salt bath. The reaction mixture was stirred at a pH level of 12.5 for 1 hour.

After that, the reaction mixture at the pH level of about 12.5 was extracted using 100 ml of ethyl acetate and dried over anhydrous sodium sulfate. After removal of solvents, thick oil was obtained. The crude free base levomethadone was treated with HCl 6M with an amount of about 0.3 ml under cooling to form levomethadone hydrochloride. After stirring at RT for 15 minutes, the solvent was removed under reduced pressure at 50° C. and then 60° C. Residual water was also removed by co-evaporation using toluene with an amount of about 0.4 ml. The resulting mixture was then co-evaporated with acetone to give the crude product as a solid.

In order to purify the levomethadone hydrochloride, the crude product was dissolved in a minimum amount of hot methanol (2 ml) and stirred with 6 ml of acetone at gentle reflux for a time period of 15 minutes. After stirring overnight at room temperature, solid precipitate with an amount of about 0.0263 gram was formed with a yield of about 91% and filtered. In the end, the solid precipitate was washed with cooled acetone and dried in a vacuum.

Figure 22:
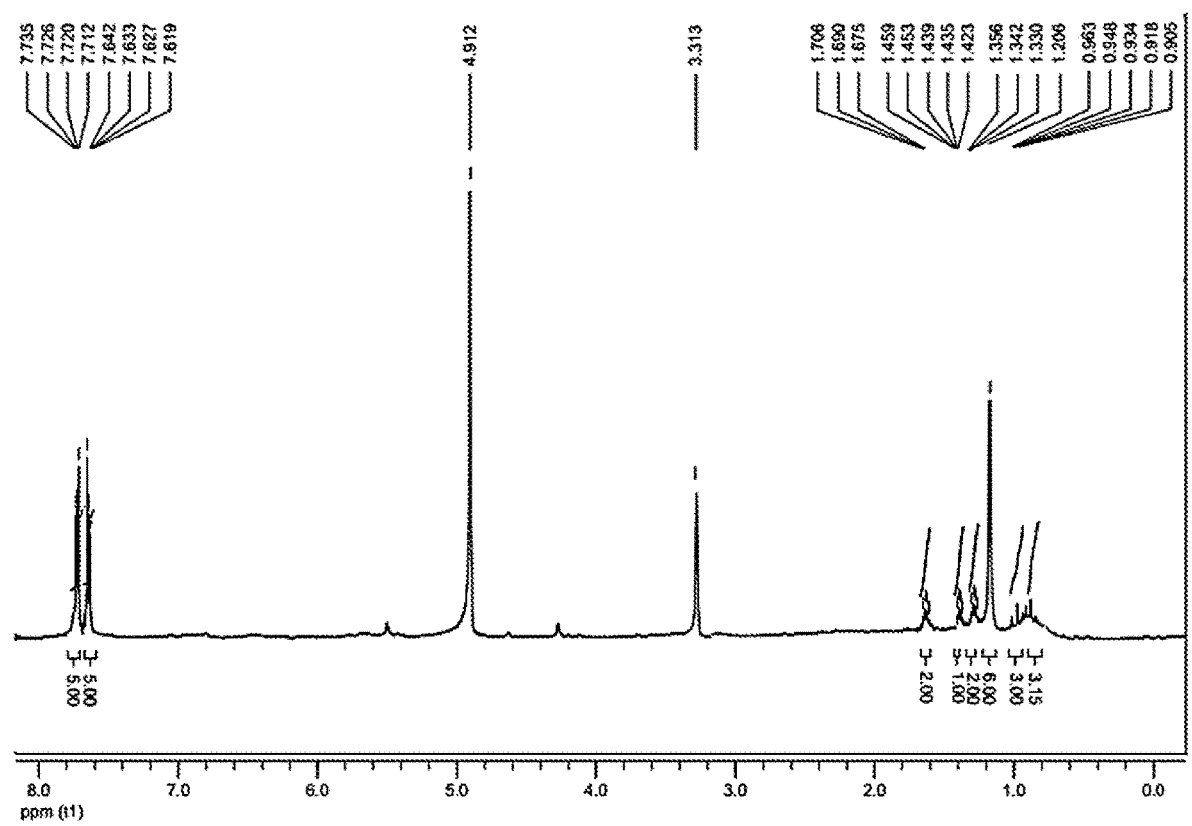
FIG. 22 illustrates a $^1$H NMR spectrum of levomethadone hydrochloride, consistent with one or more exemplary embodiments of the present disclosure.

The optical purity of levomethadone hydrochloride may be confirmed by its optical rotation. FIG. 22 shows a $^1$H NMR spectrum of levomethadone hydrochloride, consistent with one or more exemplary embodiments of the present disclosure. Referring to FIG. 22, the $^1$H NMR spectra were consistent with the proposed structure of levomethadone hydrochloride. [α]25D=−1360 (c=2.00, EtOH), Literature Data: [α] 25D=−135.4° (c=1.96, EtOH), m.p=240° C., Literature Data: m.p=240.6-241.3° C., $^1$H NMR (500 MHz. CD$_3$OD)/δ ppm: 0.90 (d, J=6.5 Hz, 3H), 0.93 (t, J=7.0 Hz, 3H), 1.20 (s, 6H), 1.33-1.35 (m, 2H), 1.42-1.46 (m, 1H), 1.67-1.70 (m, 2H), 7.62-7.64 (m, 5H), 7.71-7.73 (m, 5H) ppm.

Figure 23:
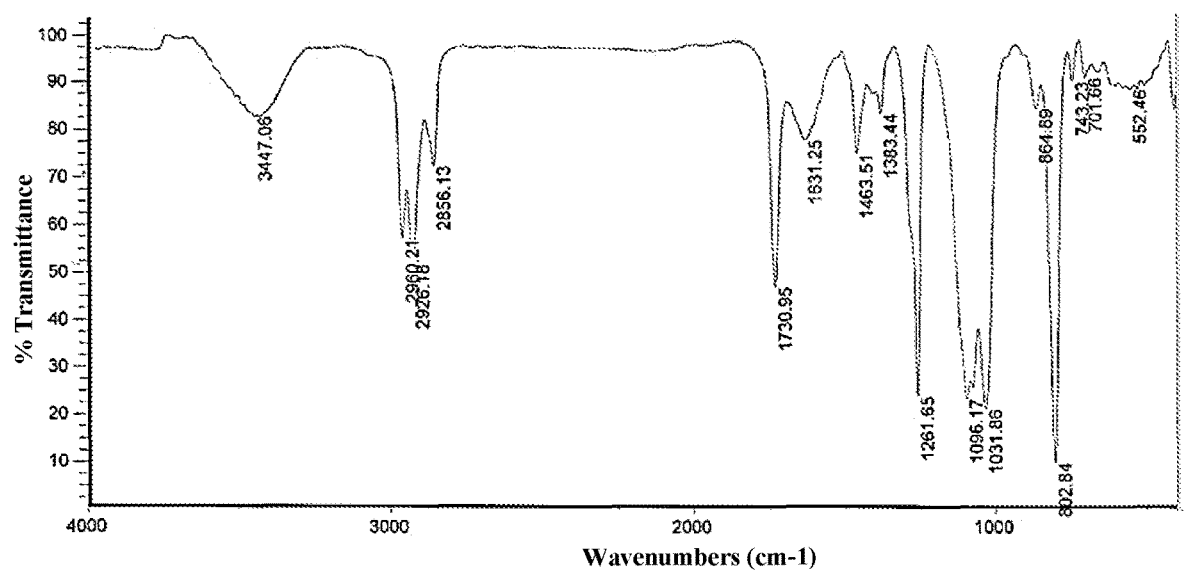
FIG. 23 illustrates an FTIR spectrum of levomethadone hydrochloride, consistent with one or more exemplary embodiments of the present disclosure.

FIG. 23 shows an FTIR spectrum of levomethadone hydrochloride, consistent with one or more exemplary embodiments of the present disclosure. Referring to FIG. 23, spectrum of levomethadone hydrochloride exhibited peaks at wavelengths 3447 cm$^{-1}$, 2960 cm$^{-1}$, 2856 cm$^{-1}$, 1730 cm$^{-1}$, 1631 cm$^{-1}$, 1463 cm$^{-1}$, 1383 cm$^{-1}$, 1261 cm$^{-1}$, 1096 cm$^{-1}$, 1031 cm$^{-1}$, 802 cm$^{-1}$, 743 cm$^{-1}$ which may be attributed to the structure of levomethadone hydrochloride.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such away. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, the inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A method for synthesizing levomethadone hydrochloride, comprising:
   producing (R)-2-(dimethylamino)propan-1-ol by reducing N,N-dimethyl-D-alanine using borax;
   forming (R)-1-chloro-N,N-dimethylpropane-2-amine hydrochloride by chlorinating the (R)-2-(dimethylamino)propan-1-ol;
   synthesizing levomethadone nitrile hydrochloride by mixing the (R)-1-chloro-N,N-dimethylpropane-2-amine and diphenylacetonitrile with potassium t-butoxide; and
   producing levomethadone hydrochloride by exposing the levomethadone nitrile hydrochloride to a Grignard reagent.

2. The method of claim 1, wherein reducing the N,N-dimethyl-D-alanine using the borax comprises:
   forming a plurality of complexes in water by adding nickel chloride hexahydrate ($NiCl_2.6H_2O$) to a solution of the N, N-dimethyl-D-alanine, the plurality of complexes comprising the N, N-dimethyl-D-alanine and the $NiCl_2.6H_2O$; and
   mixing the plurality of complexes with water and the borax, comprising:
      forming a solution by adding the plurality of complexes to the water; and
      adding the borax to the solution.

3. The method of claim 2, wherein adding the borax to the solution comprises adding borax decahydrate ($Na_2B_4O_7.10H2O$) with a concentration between 100 mM and 160 mM to the solution.

4. The method of claim 2, wherein adding the $NiCl_2.6H_2O$ to the solution of the N, N-dimethyl-D-alanine comprises adding the $NiCl_2.6H_2O$ to the solution of the N, N-dimethyl-D-alanine with a pH level between 6.8 and 7.6.

5. The method of claim 2, wherein adding the $NiCl_2.6H_2O$ to the solution of the N, N-dimethyl-D-alanine comprises mixing the $NiCl_2.6H_2O$ with the solution of N, N-dimethyl-D-alanine with a molar ratio of $NiCl_2.6H_2O$ to the N, N-dimethyl-D-alanine between 3.5 and 4.5.

6. The method of claim 2, wherein mixing the plurality of complexes with the water and the borax comprises mixing the plurality of complexes with the water and the borax at room temperature.

7. The method of claim 2, wherein mixing the plurality of complexes with the water and the borax comprises mixing the plurality of complexes with the water and the borax for a time period of between 1.5 days and 3 days.

8. The method of claim 2, wherein adding the plurality of complexes to the water comprises adding the plurality of complexes to the water with a volume ratio of the plurality of complexes to the water between 80 and 200.

9. The method of claim 2, wherein adding the plurality of complexes to the water comprises adding the plurality of complexes to the water with a pH level between 6.8 and 7.6.

10. The method of claim 1, wherein chlorinating the (R)-2-(dimethylamino)propan-1-ol comprises:
    preparing (R)-2-(dimethylamino) propane-1-ol with HCl trapped by mixing (R)-2-(dimethylamino)propan-1-ol with HCl;
    forming a first solution by dissolving the (R)-2-(dimethylamino) propane-1-ol with HCl trapped in chloroform; and
    forming a second solution by dropwise adding the first solution to a solution of thionyl chloride at room temperature.

11. The method of claim 10, wherein mixing the (R)-2-(dimethylamino)propan-1-ol with the HCl comprises mixing the (R)-2-(dimethylamino)propan-1-ol with a concentration between 5.2 mM and 7.2 mM with a HCl solution.

12. The method of claim 10, wherein mixing the (R)-2-(dimethylamino)propan-1-ol with the HCl comprises dropwise adding the HCl to the (R)-2-(dimethylamino)propan-1-ol at room temperature during a time period between 2 hours and 4 hours.

13. The method of claim 10, wherein dropwise adding the first solution to the solution of thionyl chloride at room temperature comprises dropwise adding the first solution to the solution of thionyl chloride, the solution of thionyl chloride comprising thionyl chloride and chloroform with a volume ratio of the thionyl chloride to the chloroform between 0.75 and 0.95.

14. The method of claim 13, wherein adding the first solution to the solution of thionyl chloride comprises adding the first solution to the solution of thionyl chloride with a volume ratio of the first solution to the solution of thionyl chloride between 0.7 and 0.9 for a time period between 30 minutes and 60 minutes under a nitrogen atmosphere.

15. The method of claim 1, wherein mixing the (R)-1-chloro-N,N-dimethylpropane-2-amine and the diphenylacetonitrile with the potassium t-butoxide comprises:
    forming a first mixture by mixing (R)-1-chloro-N, N-dimethylpropane-2-amine hydrochloride with dry dimethylformamide (DMF);
    forming a second mixture by dissolving the diphenylacetonitrile in the first mixture; and
    forming a third mixture by mixing the potassium t-butoxide with the second mixture.

16. The method of claim 15, wherein mixing the (R)-1-chloro-N, N-dimethylpropane-2-amine hydrochloride with the dry DMF comprises mixing the (R)-1-chloro-N, N-dimethylpropane-2-amine hydrochloride with a concentration between 50 mM and 70 mM with the dry DMF at room temperature under a nitrogen atmosphere.

17. The method of claim 15, wherein mixing the potassium t-butoxide with the second mixture comprises mixing potassium t-butoxide with a concentration between 150 mM and 300 mM with the second mixture at a temperature of 0° C. for a time period between 30 minutes and 60 minutes.

18. The method of claim 1, wherein exposing the levomethadone nitrile hydrochloride to the Grignard reagent comprises:
    preparing the Grignard reagent by reacting magnesium powder with ethyl bromide in dry tetrahydrofuran (THF); and
    forming a mixture by adding the Grignard reagent to a solution of the levomethadone nitrile hydrochloride.

19. A method for synthesizing levomethadone hydrochloride, comprising:
producing (R)-2-(dimethylamino)propan-1-ol by reducing N,N-dimethyl-D-alanine using borax, reducing the N,N-dimethyl-D-alanine using the borax comprising:
forming a plurality of complexes in water by adding nickel chloride hexahydrate ($NiCl_2.6H_2O$) to a solution of the N, N-dimethyl-D-alanine with a molar ratio of $NiCl_2.6H_2O$ to the N, N-dimethyl-D-alanine between 3.5 and 4.5, the plurality of complexes comprising the N, N-dimethyl-D-alanine and the $NiCl_2. 6H_2O$; and
mixing the plurality of complexes with water and the borax at room temperature, comprising:
forming a solution by adding the plurality of complexes to the water; and
adding the borax with a concentration between 100 mM and 160 mM to the solution;
forming (R)-1-chloro-N,N-dimethylpropane-2-amine hydrochloride by chlorinating the (R)-2-(dimethylamino)propan-1-ol;
synthesizing levomethadone nitrile hydrochloride by mixing the (R)-1-chloro-N,N-dimethylpropane-2-amine and diphenylacetonitrile with potassium t-butoxide; and
producing levomethadone hydrochloride by exposing the levomethadone nitrile hydrochloride to a Grignard reagent.

20. The method of claim 19, wherein chlorinating the (R)-2-(dimethylamino)propan-1-ol comprises:
preparing (R)-2-(dimethylamino) propane-1-ol with HCl trapped by mixing (R)-2-(dimethylamino)propan-1-ol with HCl;
forming a first solution by dissolving the (R)-2-(dimethylamino) propane-1-ol with HCl trapped in chloroform; and
forming a second solution by dropwise adding the first solution to a solution of thionyl chloride at room temperature.

* * * * *